(12) United States Patent
Knight et al.

(10) Patent No.: US 8,186,346 B2
(45) Date of Patent: May 29, 2012

(54) SELF-AUTOMATED TITRATION SYSTEM AND METHOD

(75) Inventors: Adrian Knight, Kansas City, KS (US); Paul L. Edwards, Encinitas, CA (US); Patrick Dunne, Fullerton, CA (US); Ronald F. Richard, Temecula, CA (US); Robert M. Cram, Ramona, CA (US)

(73) Assignee: Chart SeQual Technologies Inc., Dover, DE (US)

( * ) Notice: Subject to any disclaimer, the term of this patent is extended or adjusted under 35 U.S.C. 154(b) by 516 days.

(21) Appl. No.: 12/506,645

(22) Filed: Jul. 21, 2009

(65) Prior Publication Data
US 2010/0031960 A1 Feb. 11, 2010

Related U.S. Application Data

(60) Provisional application No. 61/083,129, filed on Jul. 23, 2008.

(51) Int. Cl.
*A61M 16/00* (2006.01)
*A62B 7/00* (2006.01)
*F16K 31/02* (2006.01)
(52) U.S. Cl. .............................. 128/204.23; 128/204.21
(58) Field of Classification Search ............. 128/204.18, 128/204.21, 204.22, 204.23, 204.26, 205.11, 128/205.27; 600/300, 309, 323, 529; *A61M 16/00; A62B 7/00; F16K 31/02*
See application file for complete search history.

(56) References Cited

U.S. PATENT DOCUMENTS

| | | | |
|---|---|---|---|
| 6,371,114 B1 | 4/2002 | Schmidt et al. | |
| 6,427,690 B1 | 8/2002 | McCombs et al. | |
| 6,651,658 B1* | 11/2003 | Hill et al. ................. | 128/204.23 |
| 7,222,624 B2 | 5/2007 | Rashad et al. | |
| 2002/0096174 A1 | 7/2002 | Hill et al. | |
| 2003/0005928 A1* | 1/2003 | Appel et al. ............. | 128/202.26 |
| 2006/0174876 A1 | 8/2006 | Jagger et al. | |

* cited by examiner

*Primary Examiner* — Oren Ginsberg
(74) *Attorney, Agent, or Firm* — Fred C. Hernandez; Mintz, Levin. Cohn, Ferris, Glovsky and Popeo, P.C.

(57) ABSTRACT

A method of titration using a combination continuous flow and pulse flow portable oxygen concentration system (system) with a patient includes: a) providing the system in a continuous flow mode and titrating the patient to a predetermined blood oxygen saturation using the system at one or more predetermined conditions in the continuous flow mode; b) providing the system in a pulse flow mode and titrating the patient to the same predetermined blood oxygen saturation as step a using the system at the same one or more predetermined conditions as in step a in the pulse flow mode; c) determining an Individualized Pulse Dose Equivalent (IPDE) correlation based on data obtained from steps a and b; d) providing the system with the IPDE correlation; and e) using the IPDE correlation to operate the concentrator in a more efficient manner.

15 Claims, 20 Drawing Sheets

| PRODUCT FLOW RATE (slpm) | RECOVERY (%) | PRODUCT PURITY (%) | FEED PRESSURE (psig) | VACUUM PRESSURE (psig) | FLOW RATE (slpm) | | ADIABATIC WORK (W)* | | |
|---|---|---|---|---|---|---|---|---|---|
| | | | | | COMP. | VACUUM | COMP. | VACUUM | TOTAL |
| 3.0 | 55.1 | 91.7 | 7.7 | -7.0 | 23.8 | 20.8 | 17.9 | 20.6 | 38.5 |
| 3.0 | 53.6 | 90.4 | 7.2 | -7.0 | 24.1 | 21.1 | 17.1 | 21.2 | 38.3 |
| 3.0 | 53.6 | 90.9 | 7.2 | -7.0 | 24.2 | 21.2 | 17.2 | 21.2 | 38.4 |
| 1.0 | 54.6 | 91.6 | 9.0 | -7.0 | 8.0 | 7.0 | 6.9 | 7.0 | 13.9 |
| 2.0 | 57.2 | 92.0 | 10.6 | -7.0 | 15.3 | 13.3 | 15.2 | 13.3 | 28.4 |
| 3.0 | 54.9 | 92.3 | 9.6 | -7.5 | 24.0 | 21.0 | 21.8 | 22.9 | 44.7 |
| 2.8 | 51.7 | 93.6 | 10.1 | -7.4 | 24.1 | 21.3 | 22.9 | 22.8 | 45.8 |
| 2.5 | 46.3 | 94.5 | 10.3 | -7.5 | 24.3 | 21.8 | 23.5 | 23.8 | 47.2 |
| 3.2 | 56.3 | 90.7 | 9.9 | -7.5 | 24.6 | 21.4 | 23.0 | 23.3 | 46.3 |
| 3.4 | 58.4 | 88.0 | 9.9 | -7.0 | 24.4 | 21.0 | 22.8 | 20.9 | 43.7 |
| 2.0 | 46.9 | 94.7 | 12.1 | -7.1 | 19.3 | 17.3 | 21.3 | 17.5 | 38.8 |
| 2.2 | 51.3 | 94.3 | 11.9 | -7.2 | 19.3 | 17.1 | 21.0 | 17.6 | 38.6 |
| 2.4 | 55.6 | 93.6 | 11.7 | -7.3 | 19.3 | 16.9 | 20.8 | 17.7 | 38.5 |
| 2.5 | 57.9 | 92.7 | 11.1 | -7.3 | 19.1 | 16.6 | 19.7 | 17.4 | 37.1 |
| 2.8 | 61.8 | 89.0 | 11.3 | -7.2 | 19.2 | 16.4 | 20.0 | 16.9 | 37.0 |
| 1.5 | 58.1 | 94.3 | 10.8 | -7.2 | 11.2 | 9.8 | 11.3 | 10.1 | 21.4 |
| 1.5 | 59.9 | 94.0 | 10.8 | -7.2 | 11.2 | 9.7 | 11.3 | 10.0 | 21.3 |
| 1.6 | 67.3 | 90.1 | 10.4 | -7.3 | 11.2 | 9.4 | 10.9 | 9.9 | 20.8 |
| 1.0 | 64.0 | 94.1 | 9.0 | -7.2 | 7.0 | 6.0 | 6.1 | 6.2 | 12.3 |
| 1.2 | 70.4 | 86.3 | 8.5 | -7.4 | 7.0 | 5.8 | 5.8 | 6.2 | 12.0 |
| 1.1 | 68.1 | 90.3 | 8.7 | -7.3 | 7.0 | 5.9 | 5.8 | 6.2 | 12.0 |
| 2.5 | 45.5 | 94.4 | 9.5 | -6.1 | 24.7 | 22.2 | 22.3 | 18.8 | 41.1 |
| 2.8 | 50.5 | 93.7 | 9.7 | -6.2 | 24.8 | 22.0 | 22.8 | 18.9 | 41.7 |
| 3.0 | 54.1 | 92.5 | 10.1 | -6.3 | 24.4 | 21.4 | 23.2 | 18.6 | 41.8 |
| 3.2 | 56.3 | 90.7 | 9.9 | -6.4 | 24.6 | 21.4 | 22.9 | 18.8 | 41.7 |
| 3.5 | 59.2 | 87.4 | 9.7 | -6.4 | 24.6 | 21.1 | 22.7 | 18.8 | 41.5 |
| 1.0 | 46.0 | 90.9 | 5.8 | -5.3 | 9.4 | 8.4 | 5.5 | 5.9 | 11.5 |
| 2.0 | 47.8 | 90.5 | 6.7 | -5.4 | 18.0 | 16.0 | 12.0 | 11.6 | 23.6 |
| 3.0 | 48.2 | 90.7 | 10.1 | -5.6 | 26.9 | 23.9 | 25.6 | 17.9 | 43.5 |
| 1.0 | 52.3 | 92.3 | 5.7 | -6.1 | 8.4 | 7.4 | 4.9 | 6.1 | 11.0 |
| 1.0 | 51.3 | 91.1 | 5.3 | -6.0 | 8.5 | 7.5 | 4.6 | 6.2 | 10.8 |
| 2.0 | 51.6 | 92.4 | 7.3 | -5.9 | 17.1 | 15.1 | 12.2 | 12.2 | 24.4 |
| 2.0 | 52.4 | 91.5 | 7.1 | -5.9 | 16.6 | 14.6 | 11.7 | 11.8 | 23.5 |
| 3.0 | 48.6 | 89.9 | 8.5 | -5.8 | 26.4 | 23.4 | 21.8 | 18.3 | 40.1 |
| 3.0 | 48.9 | 90.7 | 8.8 | -5.8 | 26.5 | 23.5 | 22.6 | 18.4 | 40.9 |

FIG. 15

SELF-AUTOMATED TITRATION SYSTEM AND METHOD

CROSS-REFERENCE TO RELATED APPLICATION

This application claims the benefit of provisional patent application 61/083,129, filed Jul. 23, 2008 under 35 U.S.C. 119(e). This provisional patent application is incorporated by reference herein as though set forth in full.

BACKGROUND OF THE INVENTION

The field of this invention relates to titration systems and methods for portable oxygen concentration systems.

There is a burgeoning need for home and ambulatory oxygen. Supplemental oxygen is necessary for patients suffering from lung disorders; for example, pulmonary fibrosis, sarcoidosis, or occupational lung disease. For such patients, oxygen therapy is an increasingly beneficial, life-giving development. While not a cure for lung disease, supplemental oxygen increases blood oxygenation, which reverses hypoxemia. This therapy prevents long-term effects of oxygen deficiency on organ systems—in particular, the heart, brain and kidneys.

Oxygen treatment is also prescribed for Chronic Obstructive Pulmonary Disease (COPD), and for other ailments that weaken the respiratory system, such as heart disease and AIDS. Supplemental oxygen therapy is also prescribed for asthma and emphysema.

Portable oxygen concentrators are commercially available for providing ambulatory respiratory patients with COPD and other respiratory ailments with gaseous oxygen. A portable oxygen concentrator converts ambient air into concentrated gaseous oxygen. The portable oxygen concentrator is small and light-weight, allowing the ambulatory respiratory patient to readily use and transport the portable oxygen concentrator inside and outside the home. As a result, the respiratory patient can lead a more active lifestyle, which can improve the patient's overall health.

A typical portable oxygen concentrator delivers flow at a flow rate in units of liters per minute (lpm), which is prescribed by a doctor. A Respiratory Therapist ("RT") titrates the patient to show that the prescription is correct. During the titration process, the patient is sitting at rest and the RT monitors the patient with a pulse oximeter to determine that the prescription elevated the patient's blood satuturation above 90%.

SUMMARY OF INVENTION

Accordingly, an aspect of the invention involves a semi-automated titration system and method where the patient is run through a series of steps for determining whether a portable oxygen concentrator is suitable for the patient, whether the patient can/will use a pulse flow mode, what the ideal continuous flow mode and/or pulse flow mode settings are for various conditions/environments (e.g., nocturnal/sleep, resting, ambulatory condition(s) such as casual walking and/or exercising, high altitude), and the Individualized Pulse Dose Equivalent ("IPDE") for a given flow rate and/or prescription in the continuous flow delivery mode.

Another aspect of the invention involves a method of titration using a combination continuous flow and pulse flow portable oxygen concentration system with a patient. The method includes the steps of: a) providing the portable oxygen concentration system in a continuous flow mode and titrating the patient to a predetermined blood oxygen saturation using the portable oxygen concentration system at one or more predetermined conditions in the continuous flow mode; b) providing the portable oxygen concentration system in a pulse flow mode and titrating the patient to the same predetermined blood oxygen saturation as step a using the portable oxygen concentration system at the same one or more predetermined conditions as in step a in the pulse flow mode; c) determining an Individualized Pulse Dose Equivalent (IPDE) correlation based on data obtained from steps a and b; d) providing the portable oxygen concentration system with the IPDE correlation; and e) using the IPDE correlation to operate the concentrator in a more efficient manner.

One or more implementations of the aspect of the invention described immediately above include one or more of the following: titrating the patient to a predetermined blood oxygen saturation in steps a and b is performed with a pulse oximeter; the predetermined blood oxygen saturation is at least 90% $SaO_2$; the portable oxygen concentration system weighs 4 to 20 lbs.; the one or more conditions in steps a and b is a resting condition; the one or more conditions in steps a and b is a ambulatory condition; the one or more conditions in steps a and b is a sleeping condition; and the one or more conditions in steps a and b is a high-altitude condition.

A further aspect of the invention involves a method of using a combination continuous flow and pulse flow portable oxygen concentration system with a patient. The method includes the steps of: a) sensing one or more conditions related to one or more of the patient and an environment of the patient; b) determining an Individualized Pulse Dose Equivalent (IPDE) to provide a predetermined blood oxygen saturation based on the sensed one or more conditions using an Individualized Pulse Dose Equivalent correlation; and c) supplying oxygen gas to the patient in a pulse flow mode at the IPDE to provide the predetermined blood oxygen saturation.

One or more implementations of the aspect of the invention described immediately above include one or more of the following: sensing occurs with one or more output sensors that sense one or more conditions related to one or more of the patient and an environment of the patient; the one or more output sensors include one or more of an ultrasonic flow sensor, a gas temperature sensor, an atmospheric pressure sensor, a humidity sensor, and a breath detect sensor; and the portable oxygen concentration system weighs 4 to 20 lbs.;

A still further aspect of the invention involves a combination continuous flow and pulse flow portable oxygen concentration system for use with a patient. The combination continuous flow and pulse flow portable oxygen concentration system includes a) an oxygen gas generator that separates concentrated oxygen gas from ambient air; b) an energy source that powers at least a portion of the oxygen gas generator; c) one or more output sensors that sense one or more conditions related to one or more of the patient and an environment of the patient; and d) a control unit linked to the one or more output sensors and the oxygen gas generator to control the operation of the oxygen gas generator, the control unit using a Individualized Pulse Dose Equivalent (IPDE) correlation to supply oxygen gas to the patient in a pulse flow at an Individualized Pulse Dose Equivalent (IPDE) to provide a predetermined blood oxygen saturation based on the sensed one or more conditions.

One or more implementations of the aspect of the invention described immediately above include one or more of the following: the one or more output sensors include one or more of an ultrasonic flow sensor, a gas temperature sensor, an atmospheric pressure sensor, a humidity sensor, and a breath detect sensor; and the portable oxygen concentration system weighs 4 to 20 lbs.

Other and further objects, features, aspects, and advantages of the present inventions will become better understood with the following detailed description of the accompanying drawings.

BRIEF DESCRIPTION OF THE DRAWINGS

FIG. 15 is a table of experimental data for a portable oxygen concentration system including the concentrator illustrated in FIGS. 7A and 7B.

DETAILED DESCRIPTION OF THE PREFERRED EMBODIMENT

Figure 1:
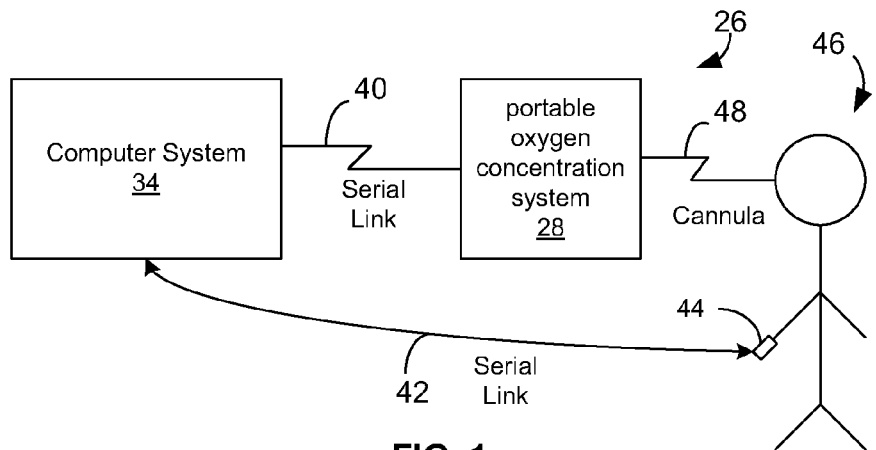
FIG. 1 is a block diagram of a semi-automated titration system in accordance with an embodiment of the invention.

With reference to FIGS. 1-4, an embodiment of a semi-automated titration system 26 and method 52 for a portable oxygen concentration system 28 will now be described. Although the semi-automated titration system 26 and method are described below in conjunction with a portable oxygen concentration system 28, in alternative embodiments, the system 26 and method may used for semi-automated titration of other types of oxygen concentration systems 28 or other types of systems.

The semi-automated titration system 26 includes a computer system 34 connected to the portable oxygen concentration system 28 via a serial link (e.g., cable, wireless connection) 40. The computer system 34 is connected to a pulse oximeter 44 via a serial link (e.g., cable, wireless connection) 42. The pulse oximeter 44 indirectly measures the blood oxygen saturation ($SaO_2$) of a patient 46. The patient 46 is an ambulatory respiratory patient that has a need for supplemental gaseous oxygen. The gaseous oxygen is delivered from the portable oxygen concentration system 28 to the patient 46 via a cannula 48. In one or more embodiments, one or more of the portable oxygen concentration system 28, the computer system 34, and the pulse oximeter 44 are integrated into a single packaged system.

Figure 2:
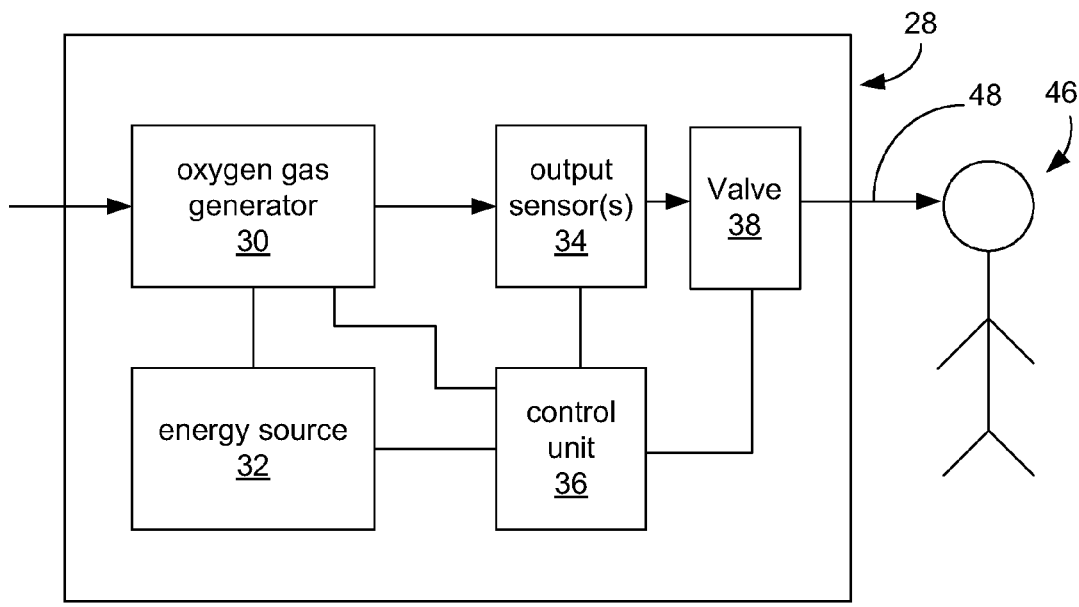
FIG. 2 is a block diagram of an embodiment of a portable oxygen concentration system of the semi-automated titration system illustrated in FIG. 1.
Figure 3:
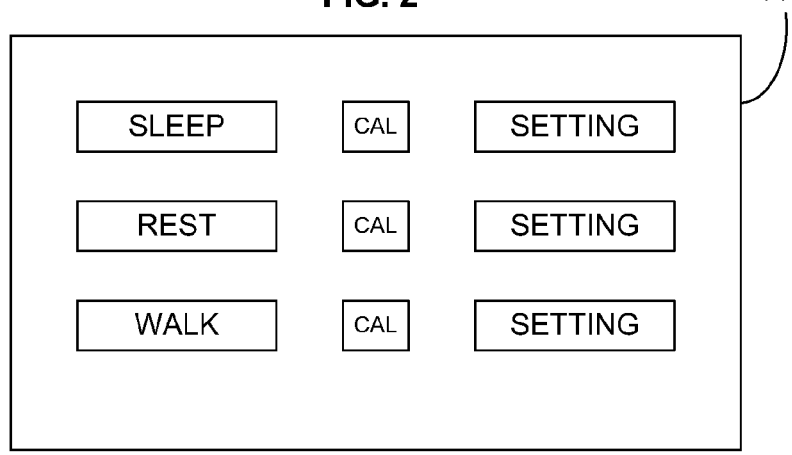
FIG. 3 is a front elevational view of an embodiment of a screen display for the computer system of the semi-automated titration system illustrated in FIG. 1.

With reference to FIG. 2, in the embodiment shown, the portable oxygen concentration system 28 is a combination continuous flow and pulse flow portable oxygen concentration system 28. An advantage of the combination continuous flow and pulse flow portable oxygen concentration system 28 is that it can generate a high flow rate of oxygen (for a portable oxygen concentrator) in the continuous flow mode for situations where a patient needs a high flow rate of oxygen gas while also meeting patient oxygen gas demand in a pulse mode, where the portable oxygen concentration system 28 conserves more energy. The combination continuous flow and pulse flow portable oxygen concentration system 28 accommodates a wide variety of ambulatory patients having different oxygen needs and accommodates a wide variety of conditions/environments/needs for a given patient. During pulse flow, a pulse of oxygen is delivered during the inspiration portion (beginning) of a breath and is not delivered when the patient is breathing out. A breath detect sensor (e.g., pressure transducer) is used to detect the beginning of the breath. Then, a pulse of a certain volume is delivered depending on the pulse flow setting (described below).

The portable oxygen concentration system 28 includes an air separation device such as an oxygen gas generator 30 that separates concentrated oxygen gas from ambient air, an energy source 32 (e.g., rechargeable battery, battery pack, fuel cell(s)) that powers at least a portion of the oxygen gas generator 30, one or more output sensors 34 used to sense one or more conditions of the patient 46, environment, etc. (e.g., ultrasonic flow sensor, gas temperature sensor, atmospheric pressure sensor, humidity sensor, breath detect sensor), a valve 38, and a control unit 36 linked to the valve 38, output sensor(s) 34, the air separation device 30, and the energy source 32 to control the operation of the air separation device 30 to deliver an optimal flow rate (lpm) and concentration of oxygen to the patient 46.

Figure 4:
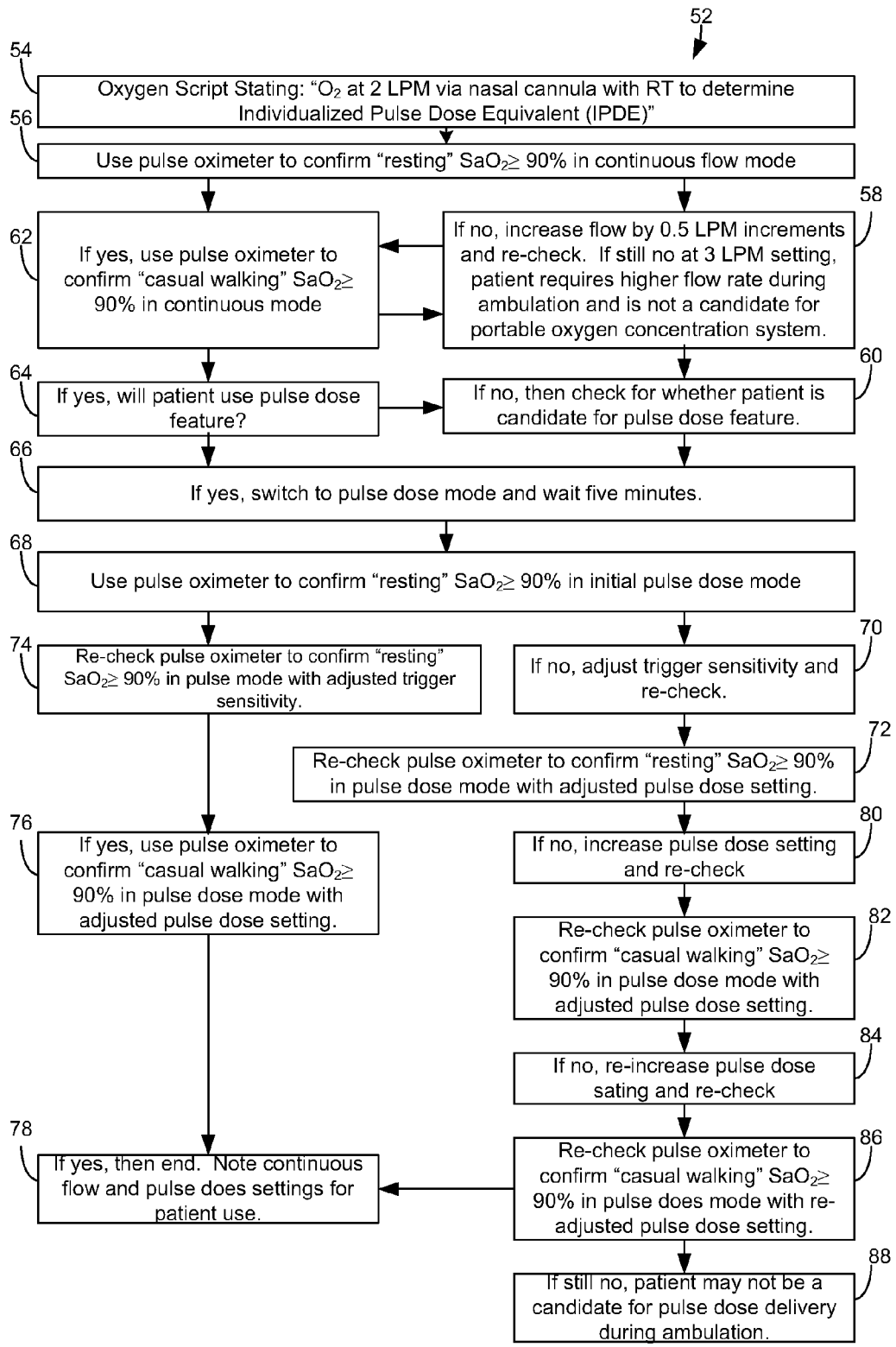
FIG. 4 is a flow chart of an exemplary semi-automated titration method in accordance with an embodiment of the invention.

With reference to FIG. 4, an exemplary semi-automated titration method 52 using the semi-automated titration system 26 will now be described. The semi-automated titration method 52 runs the patient 46 through a series of steps for determining whether a portable oxygen concentratory is suitable for the patient, whether the patient can/will use a pulse flow mode, what the ideal continuous flow mode and/or pulse flow mode settings are for various conditions/environments (e.g., nocturnal/sleep, resting, ambulatory condition(s) such as casual walking and/or exercising, high altitude), and the Individualized Pulse Dose Equivalent ("IPDE") for a given flow rate and/or prescription in the continuous flow delivery mode. IPDE is the flow setting in pulse mode that is equivalent to flow rate and/or prescription (e.g., 2 lpm) in continuous mode. In the past, it was generally believed that a fixed prescription for a patient was sufficient for ambulatory oxygen patients. For example, a fixed prescription of 2 lpm was typically prescribed in the past for ambulatory oxygen patients. However, with the portable oxygen concentration system 28, which includes both a continuous flow mode and a pulse flow mode, knowing the ideal continuous flow rate and IPDE for various conditions/environments (e.g., nocturnal/sleep, resting, ambulatory condition(s) such as casual walking and/or exercising, high altitude) allows the portable oxygen concentration system 28 to deliver the proper amount of oxygen to the patient in the most efficient manner for the condition/environment, which reduces energy consumption, increases battery life, and reduces wear in the portable oxygen concentration system 28.

First, with the patient in a resting condition (e.g., sitting on a chair), the patient 46 is connected to the system 26 and the system 26 is actuated. For example, the cannula 48 from the portable oxygen concentration system 28 is connected to the patient 46, the portable oxygen concentration system 28 is actuated, the computer system 34 runs the application(s) for the semi-automated titration method 52, and the pulse oximeter 44 is applied to the patient 46 (e.g., on the patient's finger, on the patient's ear lobe) and actuated.

Next, at step 54, a script is displayed on the screen display 50 to let the clinician and/or patient know the current function performed by the system 26. For example, an Oxygen Script Stating: "$O_2$ at 2 LPM via nasal cannula with RT to determine Individualized Pulse Dose Equivalent (IPDE)" may be displayed on screen display 50. In this example, the portable oxygen concentration system 28 is provided in a continous flow mode at a 2 LPM flow rate.

Next, at step 56, the pulse oximeter 44 measures the oxygen saturation ($SaO_2$) of the patient's blood and the system 26 confirms whether "resting" blood oxygen saturation ($SaO_2$) is greater than or equal to 90% in the continuous flow mode. In alternative embodiments, other limits other than 90% are used.

If "resting" blood oxygen saturation ($SaO_2$) is not greater than or equal to 90% in the continuous flow mode, then control passes on to step 58. At step 58, flow rate is increased by 0.5 LPM increments and the "resting" blood oxygen saturation ($SaO_2$) is re-checked. If "resting" blood oxygen saturation ($SaO_2$) is still not greater than or equal to 90% in the continuous flow mode at some maximum LPM limit for the portable oxygen concentration system 28 (e.g., 3 LPM), then the patient 46 requires higher flow rate during ambulation and is not a candidate for the portable oxygen concentration system 28. Control then passes on to step 60, and the method 52 ends.

If "resting" blood oxygen saturation ($SaO_2$) is greater than or equal to 90% in the continuous flow mode (e.g., at 2 LPM, 2.5 LPM, etc.), then the patient is instructed to perform "casual walking". Control passes on to step 62, where the pulse oximeter 44 measures the oxygen saturation ($SaO_2$) of the patient's blood and the system 26 confirms whether "casual walking" blood oxygen saturation ($SaO_2$) is greater than or equal to 90% in the continuous flow mode.

If "casual walking" blood oxygen saturation ($SaO_2$) is not greater than or equal to 90% in the continuous flow mode, then control passes to step 58. At step 58, flow rate is increased by 0.5 LPM increments and the "casual walking" blood oxygen saturation ($SaO_2$) is re-checked. At step 60, if "casual walking" blood oxygen saturation ($SaO_2$) is still not greater than or equal to 90% in the continuous flow mode at some maximum LPM limit for the portable oxygen concentration system 28 (e.g., 3 LPM), then control is passed on to steps 66/68 and the patient is checked for whether the patient is a candidate for the pulse dose feature (patient may not be recommended for continous flow, but may be recommended for pulse mode since pulse mode can produce higher saturation then continous mode). In an alternative embodiment, if "casual walking" blood oxygen saturation ($SaO_2$) is still not greater than or equal to 90% in the continuous flow mode at some maximum LPM limit for the portable oxygen concentration system 28 (e.g., 3 LPM), the patient 46 is not a candidate for the portable oxygen concentration system 28 and the method 52 ends.

If "casual walking" blood oxygen saturation ($SaO_2$) is greater than or equal to 90% in the continuous flow mode (e.g., at 2 LPM, 2.5 LPM, etc.), then control passes on to step 64, where a determination is made as to whether the patient 46 will use the pulse dose mode/feature of the portable oxygen concentration system 28. If the patient 46 will not use the pulse dose mode/feature of the portable oxygen concentration system 28, control then passes on to step 60, and the method 52 ends. If the patient 46 will use the pulse dose mode/feature of the portable oxygen concentration system 28, control then passes on to step 66, where the portable oxygen concentration system 28 is switched/provided in a pulse dose mode and the patient 46 is provided in a "resting" condition, which may include waiting for a period of time (e.g., 5 minutes) for the patient 46 to rest after "casual walking."

After switching to pulse mode, the trigger sensitivity may be adjusted/determined manually by the RT or automatically by the computer system 34. The trigger sensitivity is the value of a pressure signal used by the software to detect a breath (the system sends a pulse when this value is reached). This value can be adjusted to make it easier or harder to trigger a breath. In one embodiment, the RT verifies that when the patient breaths, the system 28 is triggered to deliver oxygen. If the RT notices that the system 28 is not delivering oxygen when the patient breaths, the trigger sensitivity is adjusted until the system 28 delivers oxygen when the patient breaths. Thus, the RT observes the patient breathing and adjusts the sensitivity of the trigger point to minimize the work of breathing and synchronize the breathing pattern of the patient with the delivery of oxygen on a breath-to-breath basis. Alternatively, as indicated above, the trigger sensitivity is adjusted/determined automatically by the computer system 34.

Then, at step 68, the pulse oximeter 44 measures the oxygen saturation ($SaO_2$) of the patient's blood and the system 26 confirms whether "resting" blood oxygen saturation ($SaO_2$) is greater than or equal to 90% in an initial pulse dose mode. As indicated above, in alternative embodiments, other limits other than 90% are used.

If "resting" blood oxygen saturation ($SaO_2$) is not greater than or equal to 90% in the initial pulse dose mode, then control passes on to step 70, where trigger sensitivity is adjusted (or re-adjusted). The "resting" blood oxygen saturation ($SaO_2$) is then re-checked. If "resting" blood oxygen saturation ($SaO_2$) is still not greater than or equal to 90% in the initial pulse dose mode, then control passes on to step 72.

If "resting" blood oxygen saturation ($SaO_2$) is greater than or equal to 90% in the initial pulse dose mode, then control passes on to step 74, where the pulse oximeter reading is re-checked with adjusted (or re-adjusted) trigger sensitivity to confirm "resting" blood oxygen saturation (SaO2) is greater than or equal to 90% in pulse dose mode. If the re-checked pulse oximeter reading confirms "resting" blood oxygen saturation (SaO2) is greater than or equal to 90% in pulse dose mode, then the patient is instructed to perform "casual walking". Control passes on to step 76, where the pulse oximeter reading is checked to confirm "casual walking" blood oxygen saturation (SaO2) is greater than or equal to 90% in pulse dose mode (at original pulse dose setting or at adjusted pulse dose setting). If "casual walking" blood oxygen saturation (SaO2) is greater than or equal to 90% in pulse dose mode, then control passes on to step 78, where the method 52 ends.

At step 72 (and subsequent steps 80, 82, 84), the pulse dose setting is adjusted and the "resting" blood oxygen saturation ($SaO_2$) is re-checked at the adjusted pulse dose setting. For example, but not by way of limitation, the portable oxygen concentration system 28 may have the following pulse dose settings: 1.0 setting=16 ml pulse bolus volume, 2.0 setting=32 ml pulse bolus volume, 3.0 setting=48 ml pulse bolus volume, 4.0 setting=64 ml pulse bolus volume, 5.0 setting=80 ml pulse bolus volume, 6.0 setting=96 ml pulse bolus volume, 7.0 setting=112 ml pulse bolus volume, 8.0 setting=128 ml pulse bolus volume, 9.0 setting=144 ml pulse bolus volume, 10.0 setting=160 ml pulse bolus volume, 11.0 setting=176 ml pulse bolus volume, 12.0 setting=192 ml pulse bolus volume. Thus, as the pulse dose setting is adjusted to a higher setting, the pulse dose volume of concentrated oxygen gas increases. Adjusting the pulse dose setting may include adjusting the pulse dose setting to the next highest setting (e.g., adjusting 1.0 setting to 2.0 setting, adjusting 2.0 setting to 3.0 setting, etc.). If the re-checked pulse oximeter reading confirms "resting" blood oxygen saturation (SaO2) is greater than or equal to 90% in pulse dose mode, then the patient is instructed to perform "casual walking" and control passes on to step 86.

At step 86, the pulse oximeter reading is checked to confirm "casual walking" blood oxygen saturation (SaO2) is greater than or equal to 90% in adjusted pulse dose setting. If "casual walking" blood oxygen saturation (SaO2) is greater than or equal to 90% in pulse dose mode, then control passes on to step 78, where the method 52 ends. If "casual walking" $SaO_2$ is not greater than or equal to 90% in pulse dose mode, then control passes on to step 88, where a determination may be made that the patient 46 is not a candidate for pulse dose delivery during ambulation.

The method 52 may include or continue with checking other conditions/environments (e.g., nocturnal/sleep, exercising, high altitude). At the end of the method 52, continuous flow settings and pulse dose settings for the patient 46 at the various conditions/environments (e.g., nocturnal/sleep, resting, ambulatory condition(s) such as casual walking and/or exercising, high altitude) are noted and/or recorded and an IPDE is determined for a give continuous flow setting and condition/environment.

In a further embodiment, the continuous flow settings and the corresponding pulse dose settings for the patient 46 at the various conditions/environments are programmed into the portable oxygen concentration system 28.

In a further embodiment, the method 52 may include additional and/or different steps and/or modes.

Further, the method 52 may be performed in a different order than that shown and described herein. For example, but not by way of limitation, the continuous flow setting and corresponding pulse dose setting for the "resting" mode may be determined first, followed by the continuous flow setting and corresponding pulse dose setting for the "casual walking" mode.

In one or more embodiments, the portable oxygen concentration system 28 includes one or more of the features shown and described below with respect to sections I to V and FIGS. 5-20. In a preferred embodiment, the portable oxygen concentration system 28 weighs 4 to 20 lbs.

I. Portable Oxygen Concentration System

Figure 5:
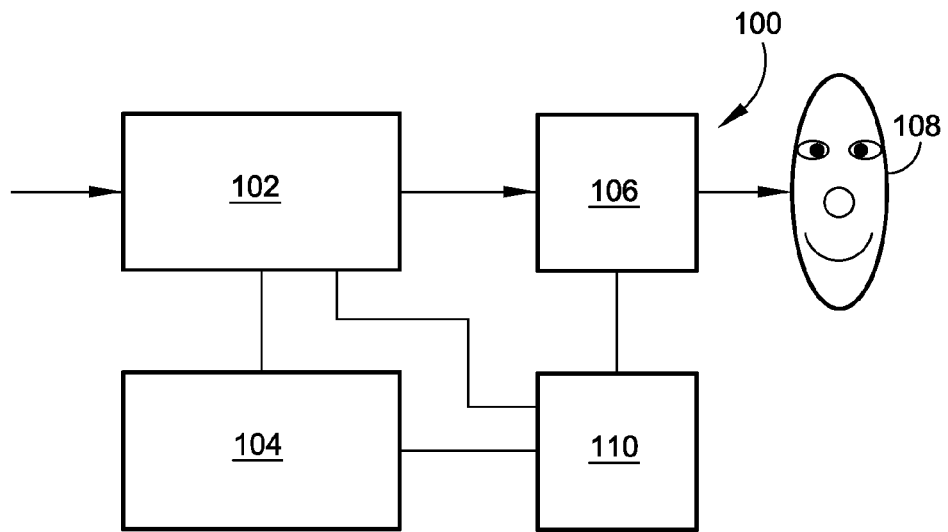
FIG. 5 is a block diagram of another embodiment of a portable oxygen concentration system constructed in accordance with an embodiment of the invention.

With reference to FIG. 5, a portable oxygen concentration system, indicated generally by the reference numeral 100, constructed in accordance with an embodiment of the invention will now be described. The oxygen concentration system 100 includes an air separation device such as an oxygen gas generator 102 that separates concentrated oxygen gas from ambient air, an energy source such as rechargeable battery, battery pack, or fuel cell 104 that powers at least a portion of the oxygen gas generator 102, one or more output sensors 106 used to sense one or more conditions of the user 108, environment, etc. to determine the oxygen output needed by the user or required from the system 100, and a control unit 110 linked to the output sensor 106, the air separation device 102, and the energy source 104 to control the operation of the air separation device 102 in response to the one or more conditions sensed by the one or more output sensors 106.

In an alternative embodiment, the system 100 may not include the one or more output sensors 106 coupled to the control unit 110. In this embodiment, conditions of the system 100 such as flow rate, oxygen concentration level, etc. may be constant for the system or may be manually controllable. For example, the system 100 may include a user interface 111 (FIG. 18) that allows the user, provider, doctor, etc. to enter information, e.g., prescription oxygen level, flow rate, etc. to control the oxygen output of the system 100.

Each element of the system 100 will now be described in more detail.

A. Air Separation Device

Figure 6:
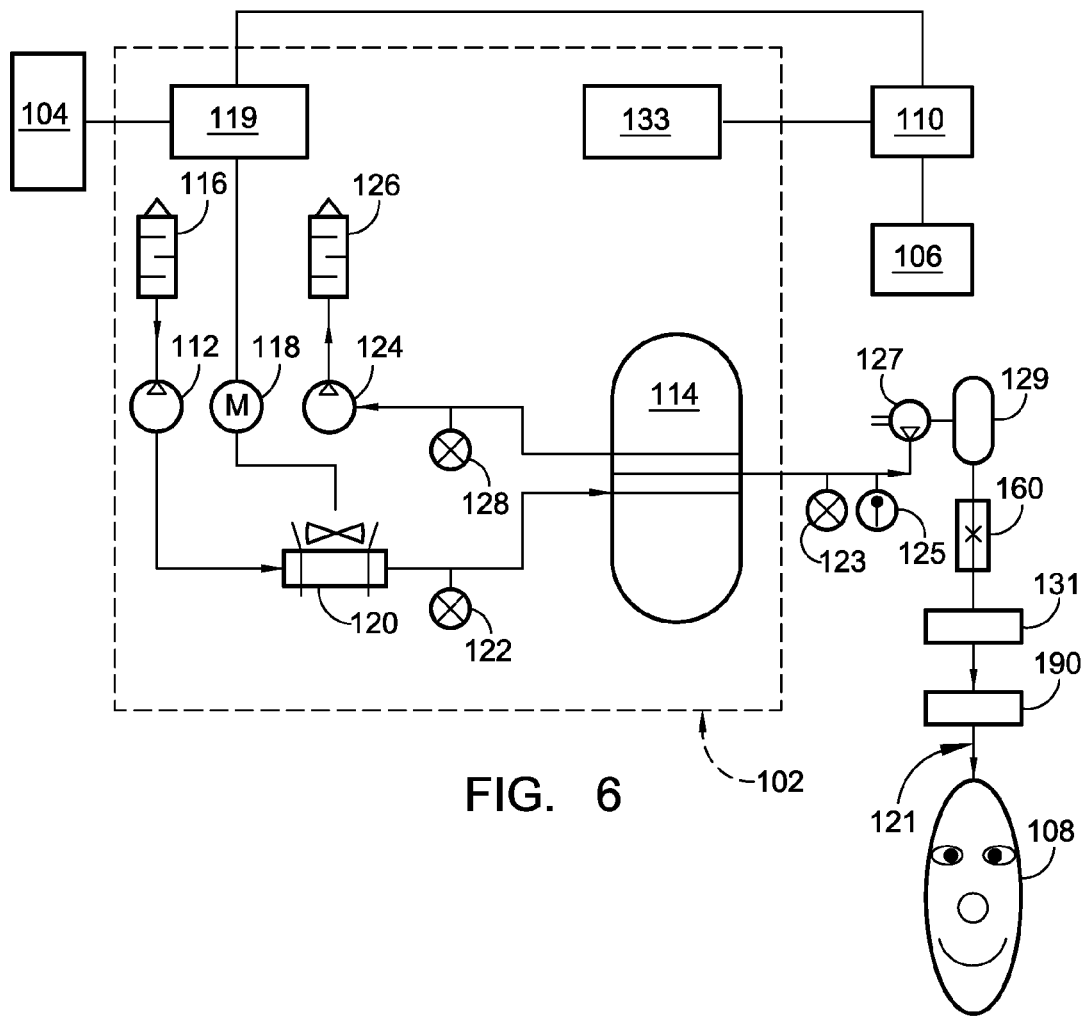
FIG. 6 is a block diagram of a portable oxygen concentration system constructed in accordance with a further embodiment of the invention, and illustrates, in particular, an embodiment of an air separation device.

With reference to FIG. 6, the air separation device is preferably an oxygen generator 102 generally including a pump such as a compressor 112 and an oxygen concentrator 114 (OC), which may be integrated.

The oxygen generator 102 may also include one or more of the elements described below and shown within the segmented boundary line in FIG. 6. Ambient air may be drawn through an inlet muffler 116 by the compressor 112. The compressor 112 may be driven by one or more DC motors 118 (M) that run off of DC electrical current supplied by the rechargeable battery 104 (RB). The motor 118 also preferably drives the cooling fan part of the heat exchanger 120. A variable-speed controller (VSC) or compressor motor speed controller 119, which is described in more detail below, may be integral with or separate from the control unit 110 (CU) and is preferably coupled to the motor 118 for conserving electricity consumption. The compressor 112 delivers the air under pressure to the concentrator 114.

In a preferred embodiment, at a maximum speed air is delivered to the concentrator 114 at 7.3 psig nominal and may range from 5.3 to 12.1 psig. At maximum speed, the flow rate of feed is a minimum of 23.8 SLPM at inlet conditions of 14.696 psi absolute, 70 degrees F., 50% relative humidity.

A heat exchanger 120 may be located between the compressor 112 and the concentrator 114 to cool or heat the air to a desired temperature before entering the concentrator 114, a filter (not shown) may be located between the compressor 112 and the concentrator 114 to remove any impurities from the supply air, and a pressure transducer 122 may be located between the compressor 112 and the, concentrator 114 to get a pressure reading of the air flow entering the concentrator 114.

The concentrator 114 separates oxygen gas from air for eventual delivery to the user 108 in a well-known manner. One or more of the following components may be located in a supply line 121 between the concentrator 114 and the user 108: a pressure sensor 123, a temperature sensor 125, a pump 127, a low-pressure reservoir 129, a supply valve 160, a flow and purity sensor 131, and a conservation device 190. As used herein, supply line 121 refers to the tubing, connectors, etc. used to connect the components in the line. The pump 127 may be driven by the motor 118. The oxygen (gas may be stored in the low-pressure reservoir 129 and delivered therefrom via the supply line 121 to the user 108. The supply valve 160 may be used to control the delivery of oxygen gas from the low-pressure reservoir 129 to the user 108 at atmospheric pressure.

Exhaust gas may also be dispelled from the concentrator 114. In a preferred embodiment of the invention, a vacuum generator 124 (V), which may also be driven by the motor 118 and integrated with the compressor 112, draws exhaust gas from the concentrator 114 to improve the recovery and productivity of the concentrator 114. The exhaust gas may exit the system 100 through an exhaust muffler 126. A pressure transducer 128 may be located between the concentrator 114 and the vacuum generator 124 to get a pressure reading of the exhaust flow from the concentrator 114. At maximum rated speed and a flow rate of 20.8 SLPM, the pressure at the vacuum side is preferably −5.9 psig nominal and may range from −8.8 to −4.4 psig.

1. Compressor/Variable Speed Controller

Example of compressor technologies that may be used for the compressor 112 include, but not by way of limitation, rotary vane, linear piston with wrist pin, linear piston without wrist pin, nutating disc, scroll, rolling piston, diaphragm pumps, and acoustic. Preferably the compressor 112 and vacuum generator 124 are integrated with the motor 118 and are oil-less, preventing the possibility of oil or grease from entering the air flow path.

The compressor 112 preferably includes, at a minimum, a 3:1 speed ratio, with a low speed of at least 1,000 rpm and a 15,000 hour operating life when run at full speed. Operating temperature surrounding the compressor/motor system is preferably 32 to 122 degrees F. Storage temperature is preferably −4 to 140 degree F. Relative humidity is preferably 5 to 95% RH noncondensing. Voltage for the compressor 112 is preferably 12 V DC or 24V DC and the electrical power requirements are preferably less than 100 W at full speed and rated flow/nominal pressure and less than 40 W at 1/3 speed and 1/3 flow at rated pressure. A shaft mounted fan or blower may be incorporated with the compressor 112 for compressor cooling and possible complete system cooling. Preferably, the maximum sound pressure level of the compressor 112 may be 46 dBA at a maximum rated speed and flow/pressure and 36 dBA at 1/3 rated speed. Preferably the compressor 112 weighs less than 3.5 pounds.

It is desirable for the compressor 112 to run at a variety of speeds; provide the required vacuum/pressure levels and flow rates, emit little noise and vibration, emit little heat, be small, not be heavy, and consume little power.

The variable-speed controller 119 is important for reducing the power consumption requirements of the compressor 112 on the rechargeable battery 104 or other energy source. With a variable-speed controller, the speed of the compressor 112 may be varied with the activity level of the user, metabolic condition of the user, environmental condition, or other condition indicative of the oxygen needs of the user as determined through the one or more output sensors 106.

For example, the variable-speed controller may decrease the speed of the motor 118 when it is determined that the oxygen requirements of the user 108 are relatively low, e.g., when the user is sitting, sleeping, at lower elevations, etc., and increased when it is determined that the oxygen requirements of the user 108 are relatively high or higher, e.g., when the user stands, when the user is active, when the user is at higher elevations, etc. This helps to conserve the life of the battery 104, reduce the weight and size of the battery 104, and reduce the compressor wear rate, improving its reliability.

The variable-speed controller 119 allows the compressor 112 to operate at a low average rate, typically the average rate or speed will be between full speed and 1/6 full speed of the compressor 112, resulting in an increase in battery life, decrease in battery size and weight, and decrease in compressor noise and emitted heat.

2. Concentrator

In a preferred embodiment, the concentrator 114 is an Advanced Technology Fractionator (ATF) that may be used for medical and industrial applications. The ATF may implement a pressure swing adsorption (PSA) process, a vacuum pressure swing adsorption (VPSA) process, a rapid PSA process, a very rapid PSA process or other process. If a PSA or VPSA process is implemented, the concentrator may include a rotating valve or a non-rotating valve mechanism to control air flow through multiple sieve beds therein. The sieve beds may be tapered so that they have larger diameter where gaseous flow enters the beds and a smaller diameter where gaseous flow exits the beds. Tapering the sieve beds in this manner requires less sieve material and less flow to obtain the same output.

Although an ATF concentrator 114 is used in a preferred embodiment, it will be readily apparent to those skilled in the art that other types of concentrators or air-separation devices may be used such as, but not by way of limitation, membrane separation types and electrochemical cells (hot or cold). If other types of concentrators or air-separation devices are used, it will be readily apparent to those skilled in the art that some aspects described herein may change accordingly. For example, if the air-separation device is a membrane separation type, pumps other than a compressor may be used to move air through the system.

The ATF preferably used is significantly smaller that ATFs designed in the past. The inventors of the present invention recognized that reducing the size of the ATF concentrator 114 not only made the system 100 smaller and more portable, it also improved the recovery percentage, i.e., the percentage of oxygen gas in air that is recovered or produced by the concentrator 114 and the productivity (liters per minute/lb. of sieve material) of the concentrator 114. Reducing the size of the ATF decreases the cycle time for the device. As a result, productivity is increased.

Further, finer sieve materials increase recovery rates and productivity. The time constant to adsorb unwanted gases is smaller for finer particles because the fluid path is shorter for the gases than for larger particles. Thus, fine sieve materials having small time constants are preferred. An example of a sieve material that may be used in the ATF concentrator 114 is LithiumX Zeolite that allows for a high exchange of Lithium ions. The bead size may, for example, be 0.2-0.6 mm. In an alternative embodiment, the Zeolite may be in the form of a rigid structure such as an extruded monolith or in the form of rolled up paper. In this embodiment, the Zeolite structure would allow for rapid pressure cycling of the material without introducing significant pressure drop between the feed and product streams.

The size of the concentrator 114 may vary with the flow rate desired. For example, the concentrator 114 may come in a 1.5 Liter per minute (LPM) size, a 2 LPM size, a 2.5 LPM size, a 3 LPM size, etc.

The oxygen gas generator 102 may also include an oxygen source in addition to the concentrator 114 such as, but not by way of limitation, a high-pressure oxygen reservoir, as described in more detail below.

An ATF valve controller 133 may be integral with or separate from the control unit 110 and is coupled with valve electronics in the concentrator 114 for controlling the valve(s) of the concentrator 114.

The concentrator may have one or more of the following energy saving modes: a sleep mode, a conserving mode, and an active mode. Selection of these modes may be done manually by the user 108 or automatically such as through the described one or more sensors 106 and control unit 110.

Figure 7A:
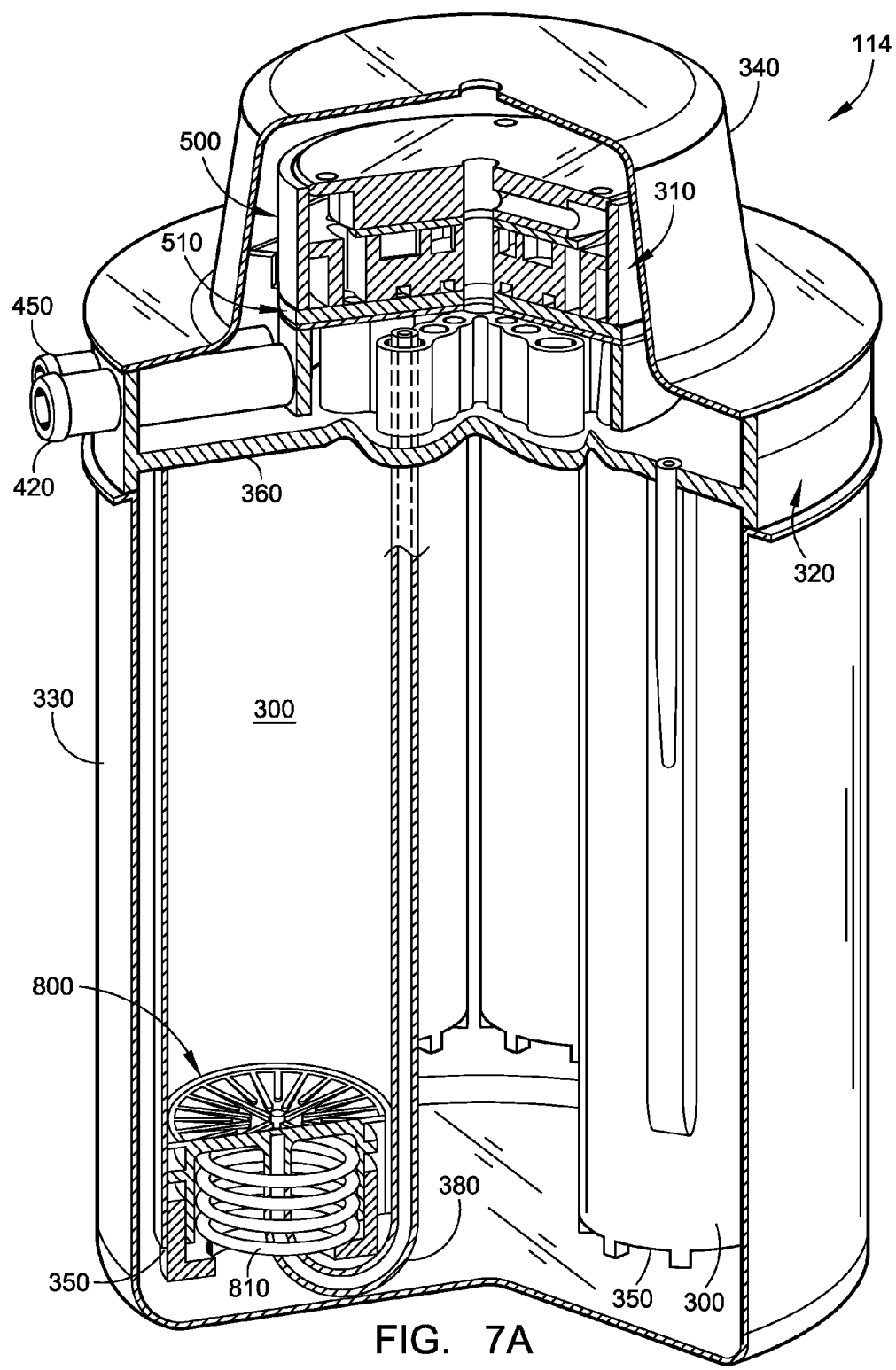
FIG. 7A is a perspective, cut-away view of an embodiment of a concentrator that may be used with the portable oxygen concentration system.
Figure 7B:
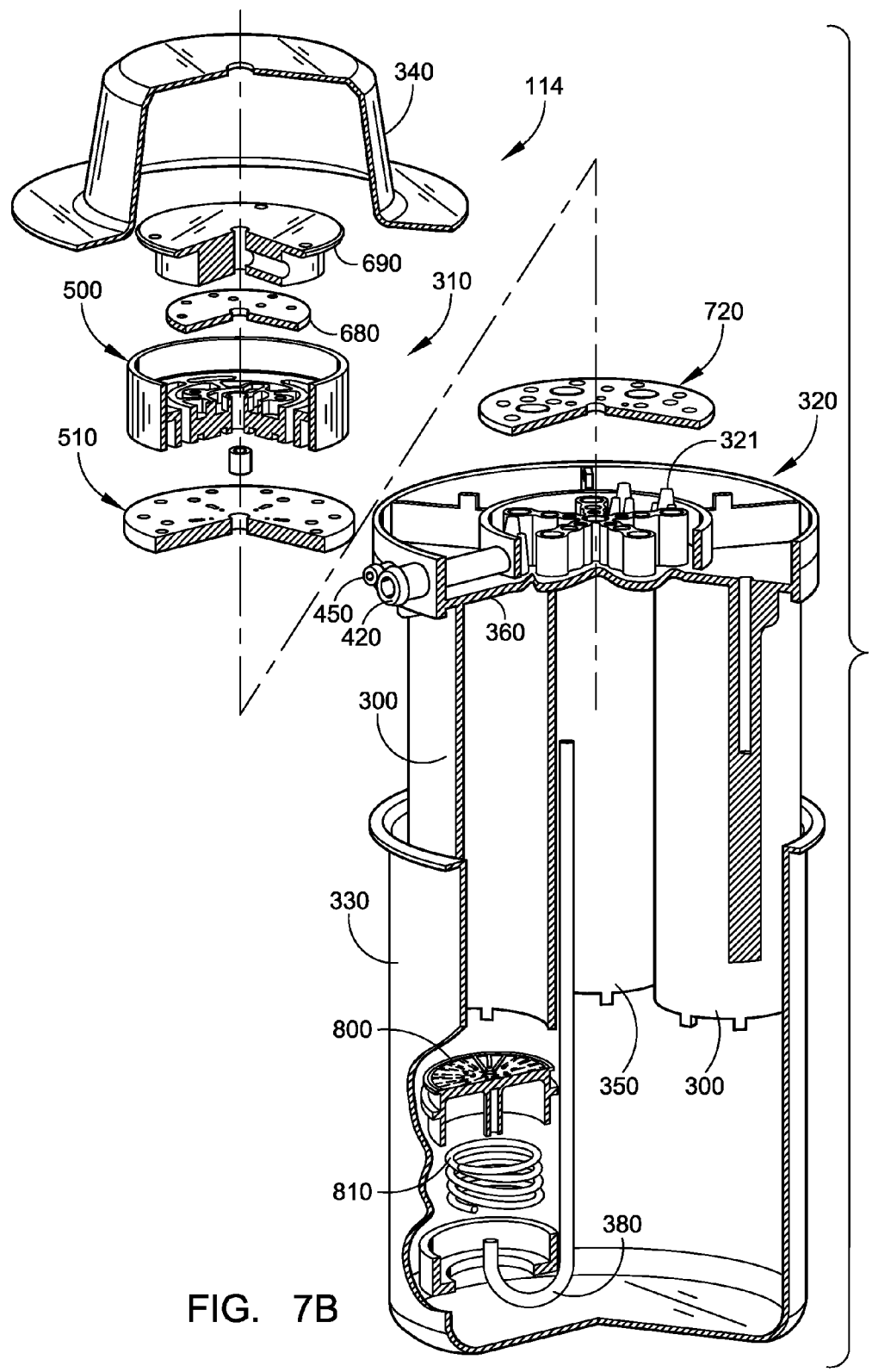
FIG. 7B is a perspective, exploded view of the concentrator illustrated in FIG. 7A.

With reference to FIGS. 7A and 7B, an embodiment of a concentrator 114 that may be used in the oxygen generator 102 will now be described in more detail. Although the concentrator 114 will be described as separating oxygen from air, it should be noted that the concentrator 114 may be used for other applications such as, but not by way of limitation, air separations for the production of nitrogen, hydrogen purification, water removal from air, and argon concentration from air. As used herein, the term "fluids" includes both gases and liquids.

The concentrator 114 described below includes numerous improvements over previous concentrators that result in increased recovery of the desired component and increased system productivity. Improved recovery is important since it is a measure of the efficiency of the concentrator. As a concentrator's recovery increases, the amount of feed gas required to produce a given amount of product decreases. Thus, a concentrator with higher recovery may require a smaller feed compressor (e.g., for oxygen concentration from air) or may be able to more effectively utilize feed gas to recover valuable species (e.g., for hydrogen purification from a reformate stream). Improved productivity is important since an increase in productivity relates directly to the size of the concentrator. Productivity is measured in units of product flow per mass or volume of the concentrator. Thus, a concentrator with higher productivity will be smaller and weigh less than a concentrator that is less productive, resulting in a more attractive product for many applications. Therefore, concentrator improvements in recovery, productivity, or both are advantageous. The specific improvements that lead to improved recovery and productivity are detailed below.

The concentrator 114 includes five adsorption beds 300, each containing a bed of adsorbent material which is selective for a particular molecular species of fluid or contaminant, a rotary valve assembly 310 for selectively transferring fluids through the adsorption beds 300, an integrated tube-assembly and mainifold "manifold" 320, a product tank cover 330, and a valve assembly enclosure 340.

The adsorption beds 300 are preferably straight, elongated, molded, plastic vessels surrounded by the product tank cover 330, which is made of metal, preferably aluminum. The molded, plastic adsorption beds 300 surrounded by the metal cover 330 make for a low-cost design without the detrimental effects of water influx that occur with prior-art plastic housings or covers. Plastic adsorption beds have the inherent problem of the plastic being permeable to water. This allows water to penetrate into the adsorbent material, decreasing the performance of the adsorbent material. Surrounding the plastic adsorption beds 300 with the aluminum cover 330, which also may serve as a product accumulation tank, maintains the low cost of the design and does not sacrifice performance.

Figure 8:
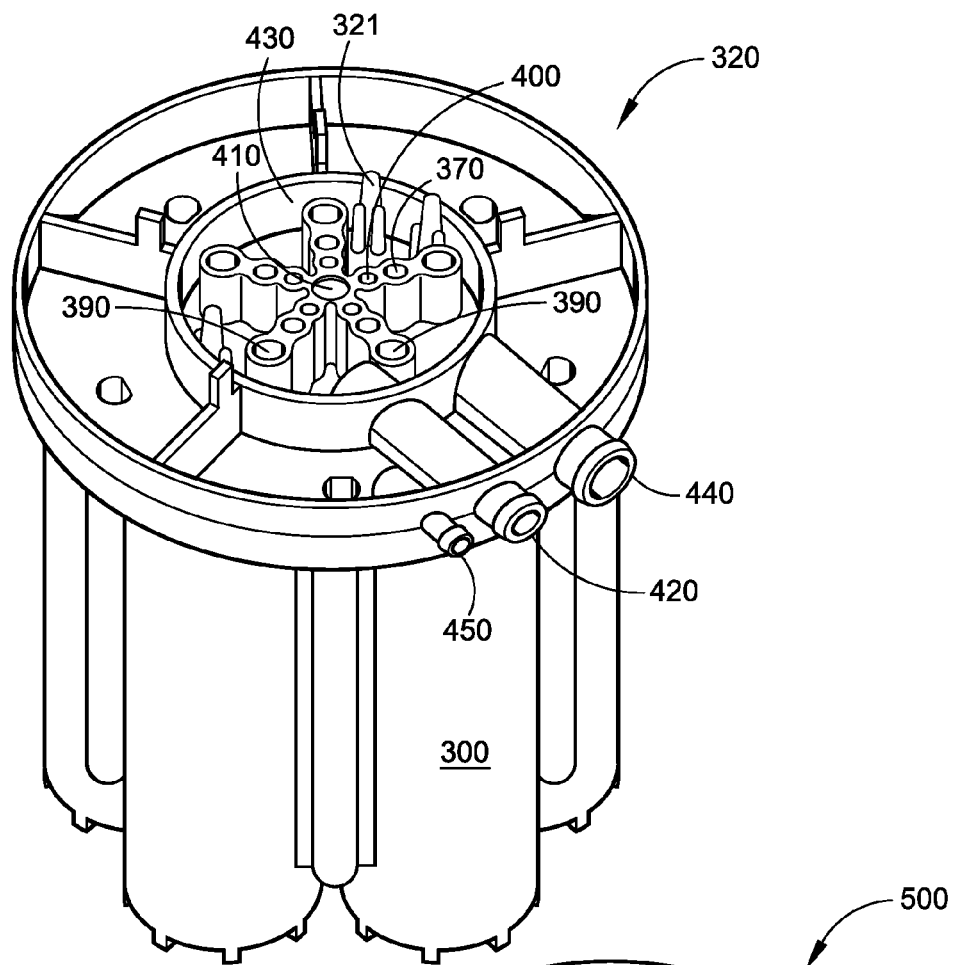
FIG. 8 is a top perspective view of an embodiment of a top manifold and multiple adsorption beds that may be used with the concentrator illustrated in FIGS. 7A and 7B.

Each adsorption bed 300 includes a product end 350 and a feed end 360. With reference additionally to FIG. 8, the product ends 350 of the beds 300 communicate with incoming product passages 370 of the manifold 320 through product lines 380 for communication with the rotary valve assembly 310. The feed ends 360 of the beds 300 communicate with outgoing feed passages 390 of the manifold 320 for communication with the rotary valve assembly 310.

The manifold 320 may also include outgoing product passages 400 that communicate the rotary valve assembly 310 with the interior of the product tank 330, an incoming feed passage 410 that communicates the rotary valve assembly 310 with a feed pressure line 420, and a vacuum chamber 430 that communicates the rotary valve assembly 310 with a vacuum pressure line 440. A product delivery line 450, which may be the same as the supply line 121 described above with respect to FIG. 6, communicates with the interior of the product tank 330. The vacuum pressure line 440 may communicate directly or indirectly with the vacuum generator 124 for drawing exhaust gas from the concentrator 114.

In use, air flows from the compressor 112 to the feed pressure line 420, through the incoming feed passage 410 of the manifold 320. From there, air flows to the rotary valve assembly 310 where it is distributed back through outgoing feed passages 390 of the manifold 320. From there, the feed air flows to the feed ends 360 of the adsorption beds 300. The adsorption beds 300 include adsorbent media that is appropriate for the species that will be adsorbed. For oxygen concentration, it is desirable to have a packed particulate adsorbent material that preferentially adsorbs nitrogen relative to oxygen in the feed air so that oxygen is produced as the non-adsorbed product gas. An adsorbent such as a highly Lithium exchanged X-type Zeolite may be used. A layered adsorbent bed that contains two or more distinct adsorbent materials may also be used. As an example, for oxygen concentration, a layer of activated alumina or silica gel used for water adsorption may be placed near the feed end 360 of the adsorbent beds 300 with a lithium exchanged X-type zeolite used as the majority of the bed toward the product end 350 to adsorb nitrogen. The combination of materials, used correctly, may be more effective than a single type of adsorbent. In an alternative embodiment, the adsorbent may be a structured material and may incorporate both the water adsorbing and nitrogen adsorbing materials.

The resulting product oxygen gas flows towards the products ends 350 of the adsorption beds 300, through the product lines 380, through incoming product passages 370 of the manifold 320, and to the rotary valve assembly 310, where it is distributed back through the manifold 320 via the outgoing product passage 400 and into the product tank 330. From the product tank 330, oxygen gas is supplied to the user 108 through the product delivery line 450 and the supply line 121.

With reference to FIGS. 7B, 9A, 9B, 10A, 12A, and 12B, an embodiment of the rotary valve assembly 310 will now be described. The rotary valve assembly 310 includes a rotary valve shoe or disk 500 and a valve port plate or disk 510. The rotary valve shoe 500 and valve port plate 510 are both preferably circular in construction and made from a durable material such as ceramic, which can be ground to a highly polished flat finish to enable the faces of the valve shoe 500 and port plate 510 to form a fluid-tight seal when pressed together.

Figure 9A:
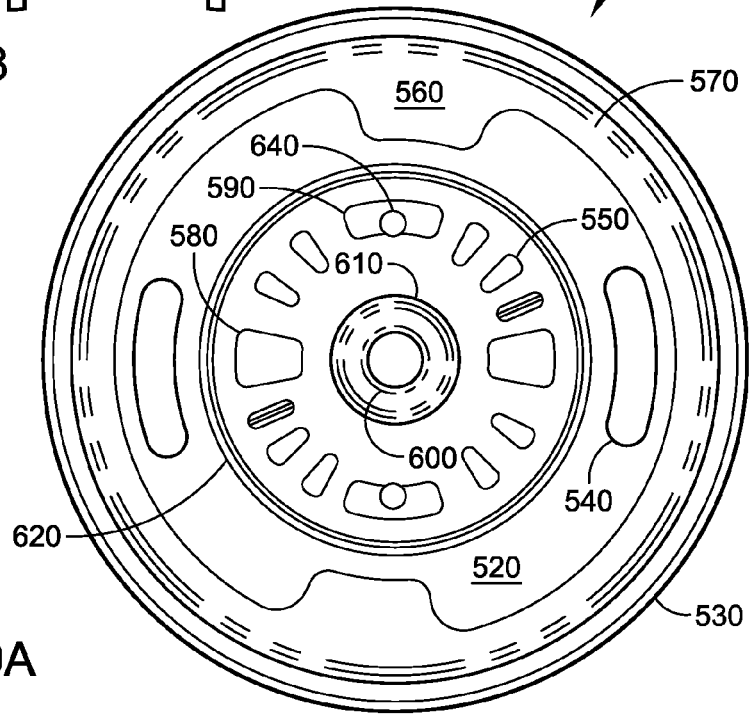
FIGS. 9A and 9B are a bottom plan view and a top plan view respectively of an embodiment of a rotary valve shoe that may be used with the concentrator illustrated in FIGS. 7A and 7B.

With reference specifically to FIG. 9A, the rotary valve shoe 500 has a flat, bottom engagement surface 520 and a smooth cylindrical sidewall 530. The valve shoe 500 has several symmetrical arcuate passages or channels cut into the engagement surface 520, all of which have as their center the geometric center of the circular engagement surface 520. The passages or channels include opposite high-pressure feed channels 540, equalization channels 550, opposite low-pressure exhaust passages 560, circular low-pressure exhaust groove 570 which communicates with exhaust passages 560, opposite product delivery channels 580, opposite purge channels 590, a high-presure central feed passage 600, a first annular vent groove 610, and a second annular vent groove 620.

Figure 9B:
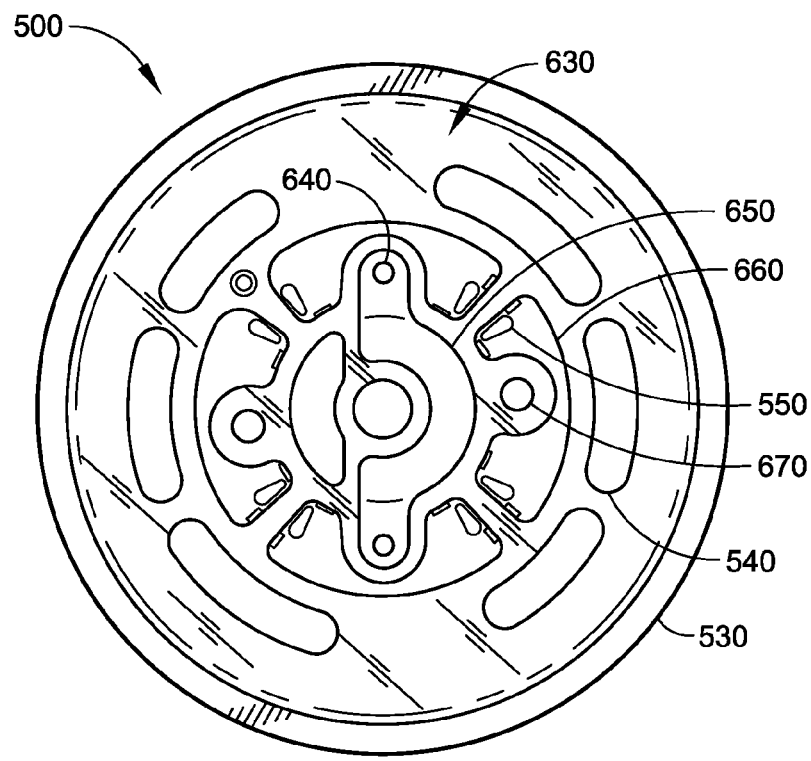

With reference additionally to FIG. 9B, a parallel, top, second valve surface 630 of the rotary valve shoe 500 will now be described. The purge channels 590 of the engagement surface 520 communicate with each other through vertical, cylindrical purge passages 640 and a rainbow-shaped purge groove 650 on the top surface 630. The equalization channels 550 of the engagement surface 520 extend vertically through the valve shoe 500. Pairs of equalization channels 550 communicate through equalization grooves 660 on the top surface 630. The equalization grooves 660 are generally U-shaped and extend around receiving holes 670. Equalization routing via the grooves 660 on the second valve surface 630, in a plane out of and parallel to a plane defined by the engagement surface 520, helps to maintain the relatively small size of the rotary valve shoe 500 while at the same time enabling more complex fluid routing through the valve shoe 500. The equalization grooves allow the secondary valve surface to be used to equalize pressures between adsorption beds 300.

Figure 12A:
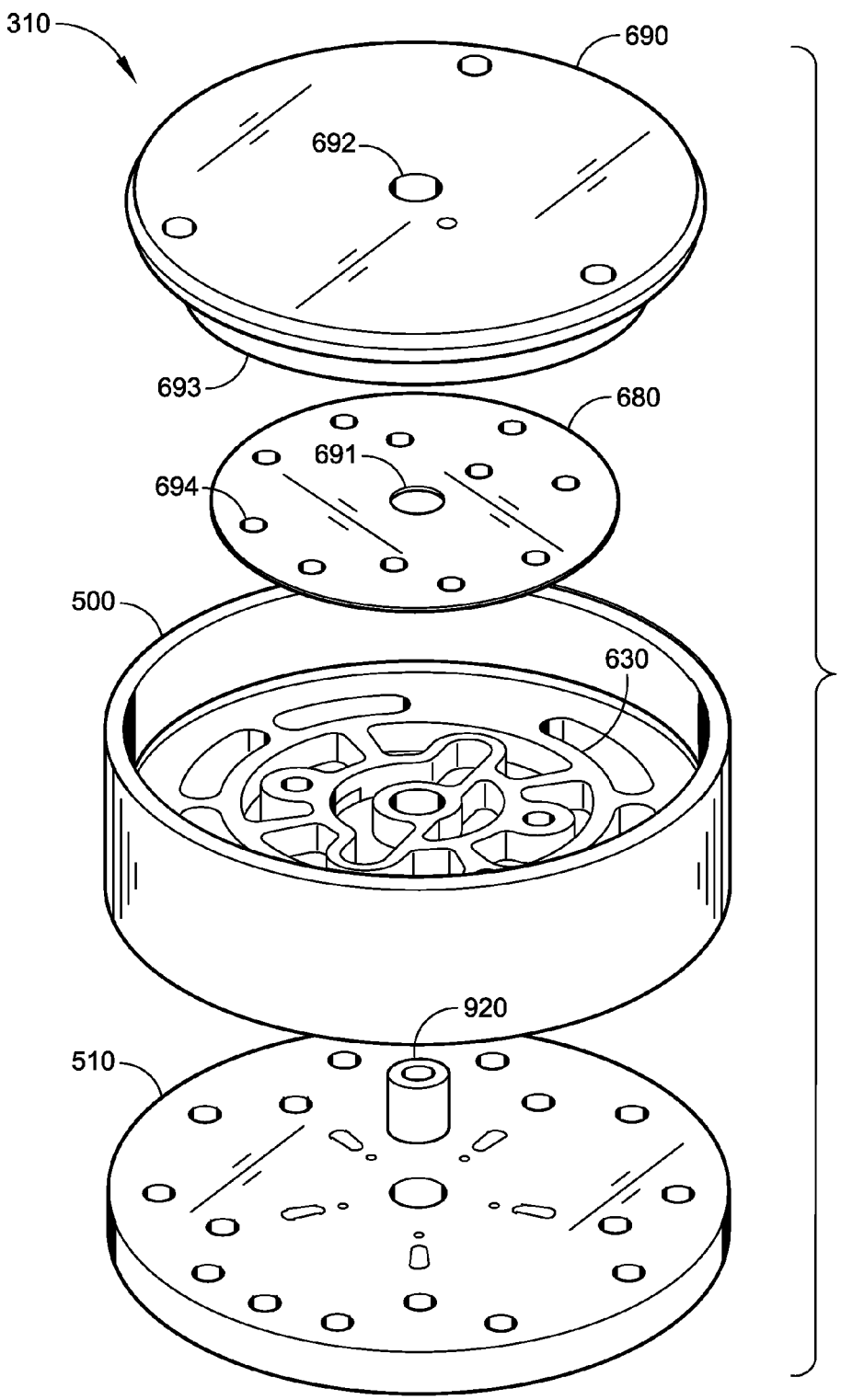
FIGS. 12A and 12B are a top perspective, exploded view and a bottom perspective, exploded view respectively of an embodiment of a rotary valve assembly including a centering pin that may be used with the concentrator illustrated in FIGS. 7A and 7B.
Figure 12B:
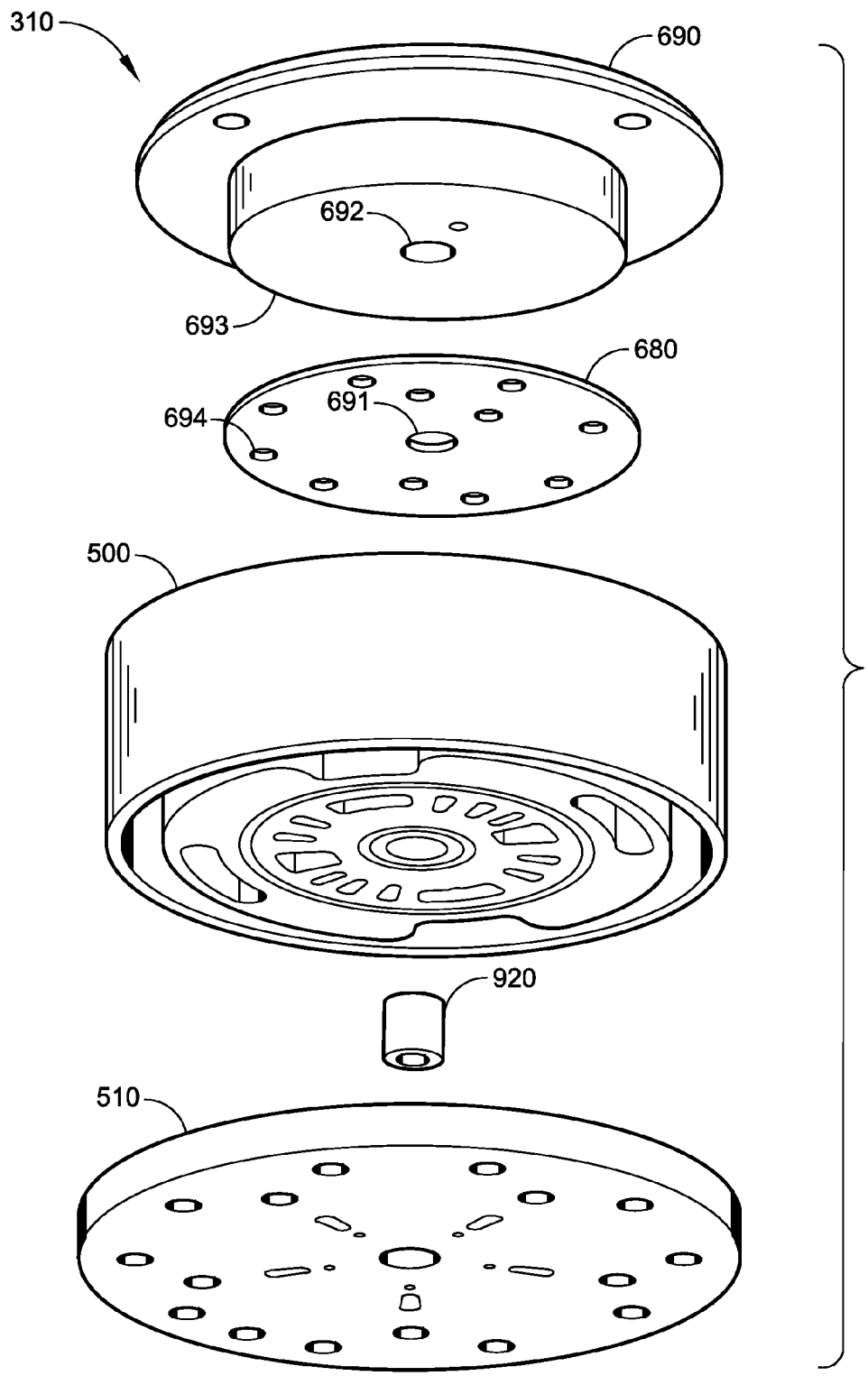

With reference to FIGS. 7B, 12A, and 12B, a first valve shoe cover 680 is disposed over the second valve surface 630 to isolate the various grooves and passages on the second valve surface 630. Both the first valve shoe cover 680 and the second valve shoe cover 690 include aligned central holes 691, 692, respectively, for communicating the central feed passage 600 with a high-pressure feed fluid chamber formed around the periphery of a cylindrical base 693 of the second valve shoe cover 690. The first valve shoe cover 680 also includes a plurality of holes 694 near its periphery for the purpose of maintaining a balance of pressure during operation on either side of the first valve shoe cover 680 between the cylindrical base 693 and the second valve surface 630. Routing the high-pressure feed fluid into the high-pressure feed fluid chamber on the top or backside of the valve shoe 500 causes pressure balancing on the valve shoe 500 that counteracts the pressure force urging the valve shoe 500 away from the port plate 510. A spring or other type of passive sealing mechanism (not shown) may be used to hold the rotary valve shoe 500 against the port plate 510 when the concentrator 114 is not operating.

With reference to FIG. 9A, to additionally counteract the pressure force that works to unseat the rotary valve shoe 500 from the port plate 510, the exhaust groove 570 is sized such that, when the concentrator 114 is operated at nominal feed and purge (vacuum) pressures, the sealing force due to the vacuum in the exhaust groove 570 subtantially balances this unseating pressure force. This enables the use of relatively small passive sealing mechanisms, reducing the torque and power required to turn the rotary valve shoe 500 and also reduces the weight and size of the concentrator 114.

Figure 10A:
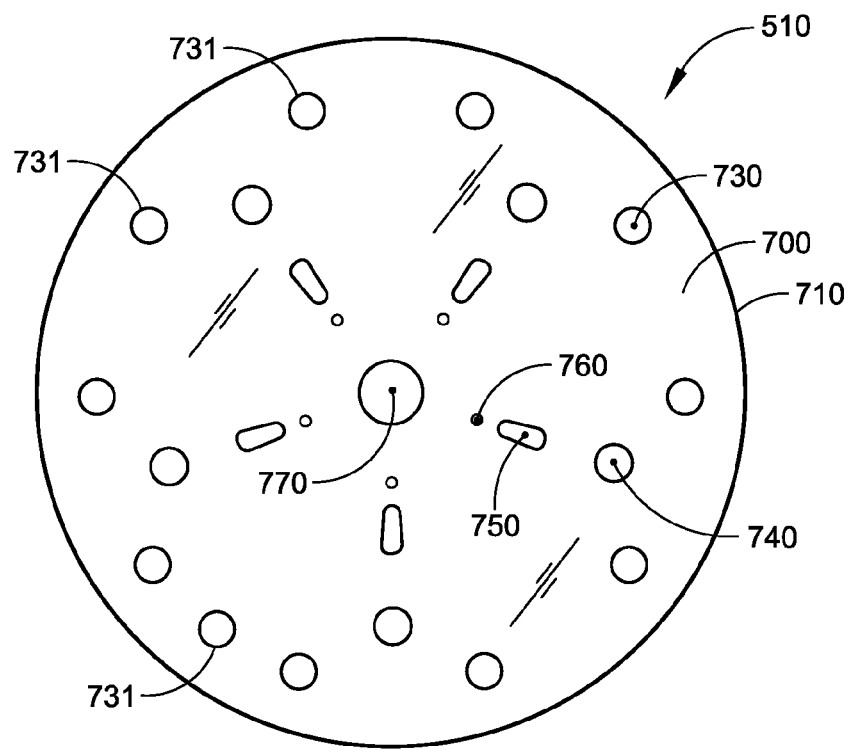
FIG. 10A is a top plan view of an embodiment of a valve port plate that may be used with the concentrator illustrated in FIGS. 7A and 7B.

With reference to FIG. 10A, the valve port plate 510 will now be described in greater detail. The valve port plate 510 has a flat engagement surface 700 that engages the flat engagement surfce 520 of the rotary valve shoe 500 and a smooth cylindrical sidewall 710. With reference additionally to FIG. 7B, an underside of the valve port plate 510 is disposed on a manifold gasket 720. The valve port plate 510 includes multiple sets of generally symmetric concentrically disposed ports or openings aligned with openings in the manifold gasket 720 to communicate the ports in the plate 510 with the passages in the manifold 320. The ports extend vertically through the valve port plate 510 in a direction generally perpendicular to the engagement surface 700. In an alternative embodiment, the ports extend vertically through the valve port plate 510 in an angular direction toward the engagement surface 700. Preferably, all of the ports of each concentric set have the same configuration. Each concentric set of ports will now be described in turn.

A first set of eight circular vacuum ports 730 concentrically disposed at a first radius from the geometric center of the valve port plate 510 communicate with the vacuum chamber 430 of the manifold 320 and the exhaust gas grooves 570 of the valve shoe 500. In the prefered embodiment, eight ports are used as they allow sufficient gas flow through the valve without significant pressure drop. In an alternative embodiment, a number of ports different from eight could be used.

A second set of five round outgoing feed ports 740 concentrically disposed at a second radius from the geometric center of the valve port plate 510 communicate with outgoing feed passages 390 of the manifold 320, the feed channels 540 of the valve shoe 500, and the vacuum ports 730 via the exhaust passages 560 of the valve shoe 500.

A third set of five generally elliptical incoming product ports 750 concentrically disposed at a third radius from the geometric center of the valve port plate 510 communicate with the incoming product passages 370 of the manifold 320, the equalization channels 550 of the valve shoe 500, the purge channels 590 of the valve shoe 500, and the product delivery channels 580.

A fourth set of five circular outgoing product ports 760 concentrically disposed at a fourth radius from the geometric center of the valve port plate 510 communicate with the outgoing product passages 400 of the manifold 320 and the incoming product ports 750 via the product delivery channels 580.

A fifth set of three circular port plate alignment holes 731 concentrically disposed at a fifth radius from the geometric center of the valve port plate 510 align with alignment pins 321 (FIGS. 7B, 8) on the manifold 320. The alignment holes 731 ensure the port plate 510 will sit in proper alignment with the manifold 320. In an alternative embodiment, two or more alignment holes located at one or more radiuses from the geometric center of the valve port plate 510 may be aligned with an equal number of alignment pins located at set positions on the manifold 320.

A round central incoming feed port 770 disposed at the geometric center of the valve port plate 510 and the center of rotation of the valve assembly 310 communicates with the incoming feed passage 410 of the manifold 320 and the central feed pasage 600 of the rotary valve shoe 500.

In the rotary valve assembly 310 described above, a maximum of 1 PSI pressure drop occurs through any port of the valve asembly 310 when the system is producing 3 LPM of oxygen product. At lesser flows, the pressure drop is negligible.

Figure 10B:
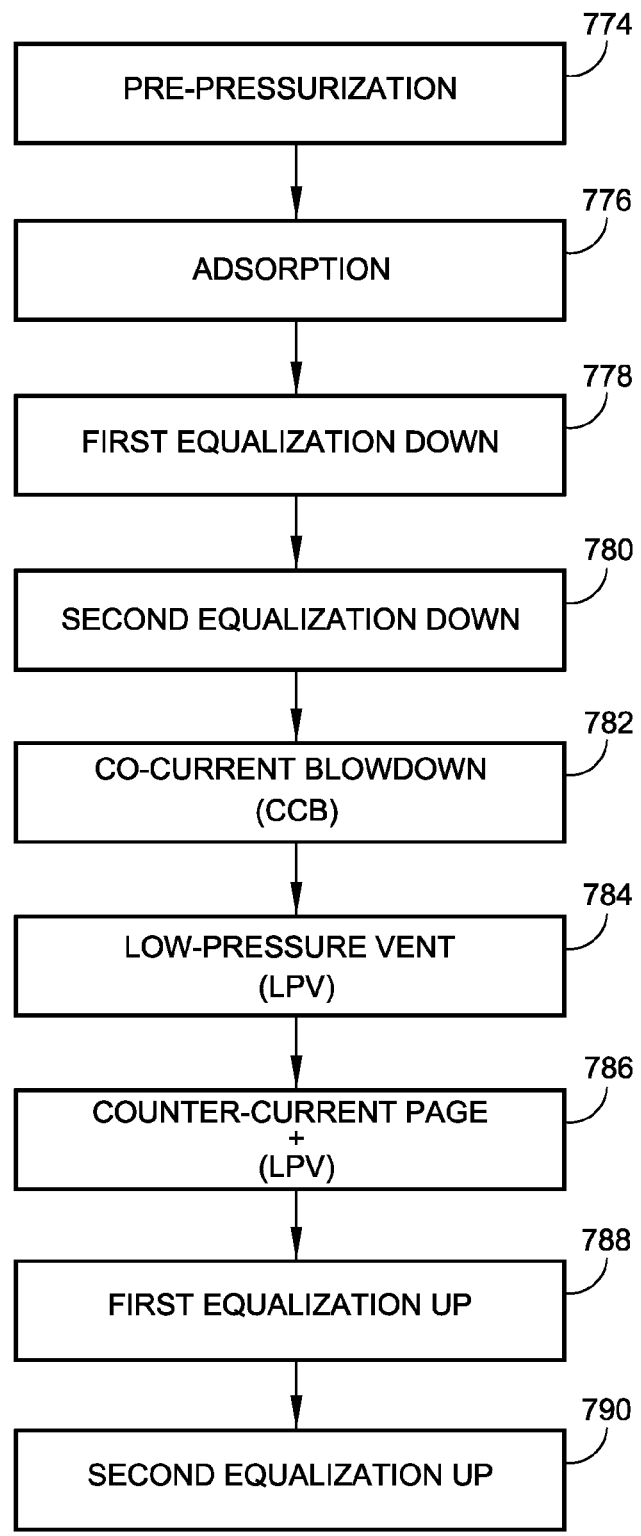
FIG. 10B is a flow chart of an exemplary process cycle for the concentrator illustrated in FIGS. 7A and 7B.

With reference additionally to FIG. 10B, a single pressure swing adsorption cycle of the concentrator 114 will now be described. During use, the rotary valve shoe 500 rotates with respect to the valve port plate 510 so that the cycle described below is sequentially and continuously established for each adsorption bed 300. The speed of rotation of the rotary valve shoe 500 with respect to the valve port plate 510 may be varied alone, or in combination with a variable-speed compressor, in order to provide the optimal cycle timing and supply of ambient air for a given production of product. To help the reader gain a better understanding of the invention, the following is a description of what occurs in a single adsorption bed 300 and the rotary valve assembly 310 during a single cycle. It should be noted, with each revolution of the rotary valve shoe 500, the adsorption beds 300 undergo two complete cycles. For each cycle, the steps include: 1) pre-pressurization 774, 2) adsorption 776, 3) first equalization down 778, 4) second equalization down 780, 5) co-current blowdown 782, 6) low-pressure venting 784, 7) counter-current purge and low-pressure venting 786, 8) first equalization up 788, and 9) second equalization up 790. Each of these steps will be described in turn below for an adsorption bed 300.

In the pre-pressurization step 774, air flows from the compressor 112 to the feed pressure line 420, through the incoming feed passage 410 of the manifold 320. From there, air flows through the central incoming feed port 770 of the port plate 510, through the central feed passage 600 and out the feed channels 540 of the valve shoe 500, through the outgoing feed ports 740, and through outgoing feed passages 390 of the manifold 320. From there, the feed air flows to the feed ends 360 of the adsorption beds 300. With reference to FIG. 9A, because the feed channel 540 is advanced with respect to the product delivery channel 580 (i.e., initially the feed channel 540 is in communication with outgoing feed port 740 and the product delivery channel 580 is blocked, not in communication with the incoming product port 750), the feed end 360 of the adsorption bed 300 is pressurized with feed gas, i.e., pressurized, prior to the commencement of product delivery. In alternative embodiments, the product end 350 may be pre-pressurized with product gas, or the product end 350 may be pre-pressurized with product gas and the feed end 360 may be pre-pressurized with feed gas.

In the adsorption step 776, because the product delivery channel 580 is in communication with the incoming product port 750, adsorption of Nitrogen occurs in the bed 300 and the resulting product oxygen gas flows towards the product ends 350 of the adsorption beds 300, through the product lines 380, and through incoming product passages 370 of the manifold 320. From there, oxygen gas flows through the incoming product port, into and out of the product delivery channel 580, through outgoing product port 760, through the outgoing product passage 400, and into the product tank 330. From the product tank 330, oxygen gas is supplied to the user 108 through the product delivery line 450 and the supply line 121.

In the first equalization-down step 778, the product end 350 of the bed 300, which is at a high pressure, is equalized with the product end of another bed, which is at a low pressure, to bring the product end 350 of the bed 300 to a lower, intermediate pressure. The product ends 350 communicate through the product lines 380, the incoming product passages 370, the incoming product ports 750, the equalization channels 550, and the equalization groove 660. As indicated above, equalization routing via the grooves 660 on the second valve surface 630, in a plane out of and parallel to a plane defined by the engagement surface 520, helps to maintain the relatively small size of the rotary valve shoe 500, in order to keep the torque required to turn the valve shoe 500 as low as possible, while at the same time enabling more complex fluid routing through the valve shoe 500. In this step 778 and the equalization steps 780, 788, 790 to be discussed below, the adsorption beds 300 may be equalized at either the feed end 360, the product end 350, or a combination of the feed end 360 and the product end 350.

In the second equalization-down step 780, the product end 350 of the bed 300, which is at an intermediate pressure, is equalized with the product end of another bed, which is at a lower pressure, to bring the product end 350 of the bed 300 further down to an even lower pressure than in step 778. Similiar to the first equalization-down step 778, the product ends 350 communicate through the product lines 380, the incoming product passages 370, the incoming product ports 750, the equalization channels 550, and the equalization groove 660.

In the co-current blowdown ("CCB") step 782, oxygen enriched gas produced from the product end 350 of the adsorption bed 300 is used to purge a second adsorption bed 300. Gas flows from the product side of the adsorption bed 300, through product line 380, incoming product passage 370, and incoming product port 750. The gas further flows through purge channel 590, purge passage 640, through the purge groove 650, out the purge passage 640 on the opposite side of the valve shoe 500, through the purge channel 590, through the incoming product port 750, through the incoming product pasasge 370, through the product line 380, and into the product end 350 of adsorption bed 300 to serve as a purge stream. In an alternative embodiment, in this step 782 and the following step 784, co-current blowdown may be replaced with counter-current blowdown.

In the low-pressure venting ("LPV") step 784, the adsorption bed 300 is vented to low pressure through the feed end 360 of the adsorption bed 300. The vacuum in the exhaust groove 570 of the rotary valve shoe 500 communicates with the exhaust passage 560 and the feed end 360 of the adsorption bed 300 (via the outgoing feed port 740 and outgoing feed passage 390) to draw the regeneration exhaust gas out of the adsorption bed 300. The low pressure venting step 784 occurs without introduction of oxygen enriched gas because the exhaust passage 560 is in communication with the outgoing feed port 740 and the purge channel 590 is not in communication with the incoming product port 750.

In the counter-current purge and low-pressure venting ("LPV") step 786, oxygen enriched gas is introduced into the product end 350 of the adsorption bed 300 in the manner described above in step 782 concurrently with the feed end 360 of the adsorption bed 300 being vented to low pressure as was described in the above step 784. Counter-current purge is introduced into the product end 350 of the adsorbent bed 300 through fluid communication with the product end 350 of a second adsorption bed 300. Oxygen enriched gas flows from the product end 350 of the second adsorption bed 300 through the product line 380, incoming product passage 370, incoming product port 750, through purge channel 590, purge passage 640, through the purge groove 650, out the purge passage 640 on the opposite side of the valve shoe 500, through the purge channel 590, through the incoming product port 750, through the incoming product passage 370, through the product line 380, and into the product end 350 of adsorption bed 300. Because the exhaust passage 560 is also in communication with the outgoing feed port 740 during this step 786, oxygen enriched gas flows from the product end 350 to the feed end 360, regenerating the adsorption bed 300. The vacuum in the exhaust groove 570 of the rotary valve shoe 500 communicates with the exhaust passage 560 and the feed end 360 of the adsorption bed 300 (via the outgoing feed port 740 and outgoing feed passage 390) to draw the regeneration exhaust gas out of the adsorption bed 300. From the exhaust passage 560, the exhaust gas flows through the vacuum ports 730, into the vacuum chamber 430, and out the vacuum presure line 440. In an alternative embodiment, the vacuum may be replaced with a low-pressure vent that is near atmospheric pressure or another pressure that is low relative to the feed pressure. In another embodiment, product gas from the product tank 330 is used to purge the product end 350 of the adsorbent bed 300.

In the first equalization-up step 788, the product end 350 of the bed 300, which is at a very low pressure, is equalized with the product end of another bed, which is at a high pressure, to bring the adsorption bed 300 to a higher, intermediate pressure. The product ends 350 communicate through the product lines 380, the incoming product passages 370, the incoming product ports 750, the equalization channels 550, and the equalization groove 660.

In the second equalization-up step 790, the product end 350 of the bed 300, which is at an intermediate pressure, is equalized with the product end of another bed, which is at a higher pressure, to bring the product end 350 of the bed 300 further up to an even higher pressure than in step 788. Similiar to the first equalization-down step 778, the product ends 350 communicate through the product lines 380, the incoming product passages 370, the incoming product ports 750, the equalization channels 550, and the equalization groove 660.

It should be noted, in a preferred embodiment, the combined duration of feed steps 774, 776 may be substantially the same as the combined duration of purge steps 782, 784, 786, which may be substantially three times the duration of each equalization step 778, 780, 788, 790. In an alternative embodiment, the relative duration of the feed steps 774, 776, the purge steps 782, 784, 786, and the each equalization step 778, 780, 788, 790 may vary.

After the second equalization-up step 790, a new cycle begins in the adsorption bed 300 starting with the pre-pressurization step 774.

The five-bed concentrator 114 and cycle described above has a number of advantages over other-numbered concentrators and cycles used in the past, some of which are described below. The multiple equalization steps 788, 790 at the product ends 350 and the pre-pressurization step 774 contribute to the pre-pressurization of the adsorption beds 300 prior to product delivery. As a result, the beds 300 reach their ultimate pressure (substantially equal to the feed pressure) quickly and thereby allow for maximum utilization of the adsorbent media. Additionally, pre-pressurizing the adsorbent beds 300 allows product to be delivered at substantially the same pressure as the feed, thereby retaining the energy of compression in the stream, which makes the product stream more valuable for use in downstream processes. In an alternative embodiment, pre-pressurizing the beds 300 with product before exposing the feed end 360 of the bed 300 to the feed stream eliminates any pressure drop experienced due to the fluid interaction or fluid communication between two or more adsorbent beds 300 on the feed end 360. Additionally, compared to systems with greater numbers of beds, the use of a 5-bed system, reduces the duration and number of beds that are in fluid communication with the feed chanels 540 at the same time, thereby reducing the propensity for fluid flow between adsorption beds. Since fluid flow between adsorption beds is associated with a reversal of the flow direction in the higher pressure bed (resulting in decreased performance), reduction in this effect is advantageous.

A further advantage of a 5-bed system over many systems is that it includes a small number of adsorption beds 300, allowing the concentrator to be relative small, compact, and light-weight, while delivering sufficient flow and purity and maintaining high oxygen recovery. Other PSA systems, typically those with a small number of adsorption beds, result in deadheading the compressor (resulting in high power use) during a portion of the cycle. Deadheading the compressor eliminates detrimental flow between the feed side 360 of the two or more adsorption beds 300 (as discussed above) but increases system power. The 5-bed system eliminates compressor deadheading and minimizes performance-limiting feed side 360 flow between adsorbent beds 300.

Use of the multiple pressure equalization steps 778, 780, 788, 790 reduces the amount of energy of compression required to operate the concentrator 114. Equalizing the beds 300 conserves high-pressure gas by moving it to another bed 300 rather than venting it to the atmosphere or to a vacuum pump. Because there is a cost associated with pressurizing a gas, conserving the gas provides a savings and improves recovery. Also, because a bed 300 may contain gas enriched with product, usually at the product end 350 of the bed 300, allowing this gas to move into another bed 300, rather than venting it, conserves product and improves recovery. The number of equalizations are preferably between one and four. It should be noted, each equalization represents two equalization steps, an equalization-down step and an equalization-up step. Thus, two equalizations means two down equalizations and two up equalizations, or four total equalizations. The same is true for other-number equalizations. In a preferred embodiment, one to four equalizations (two to eight equalization steps) are used in each cycle. In a more preferred embodiment, one to three equalizations (two to six equalization steps) are used in each cycle. In a most preferred embodiment, two equalizations (four equalization steps) are used in each cycle.

In alternative embodiments, the concentrator 114 may have other numbers of adsorption beds 300 based on the concentration of the feed stream, the specific gases to be separated, the pressure swing adsorption cycle, and the operating conditions. For example, but not by way of limitation, there also are advantages to four-bed concentrators and six-bed concentrators. When operating a cycle similar to that described above with a four-bed concentrator, the problem of fluid communication between the feed chanels 540 and more than one adsorption bed (at one instant) is completely eliminated. When the feed-end fluid communication is eliminated, the feed steps 774, 776 occur in a more desirable fashion resulting in improved recovery of the desired product. The advantages of a six-bed system, compared to a five-bed system, are realized when the pressure-swing cycle described above is modified so that there are three equalization up stages and three equalization down stages instead of two equalization up stages and two equalization down stages. A third equalization is advantageous when the feed gas is available at high pressure. The third equalization conserves compressor energy because it allows the equalized beds to obtain substantially 75% of the feed pressure compared to substantially 67% of the feed pressure when two equalization stages are used. In any PSA cycle, whenever an equalization up occurs, there is a corresponding equalization down. The requirement of matching equalization stages inparts some restrictions on the relative timing of the cycle steps. If, for example, the duration of the feed step is substantially the same as the duration of each equalization step, then a six-bed cycle would provide the required matching of equalization stages.

A number of additional inventive aspects related to the concentrator 114 that increase recovery of a desired component and system productivity will now be described. With reference to FIGS. 7A, 7B, 11A, and 11B, an embodiment of a media retention cap 800 that reduces dead volume in the adsorption beds 300 will now be described. Each media retention cap 800 is located at the product end 350 of the adsorption bed 300 and supports the adsorbent material above the media retention cap 800. A spring 810 located within and below the media retention cap 800 urges the media retention cap 800 upwards to hold the packed bed of adsorbent material firmly in place. The media retention cap 800 has a cylindrical base 820 with first and second annular flanges 830, 840. The second annular flange 840 terminates at its top in a circular rim 850. A top surface 860 of the media retention cap 800 includes a plurality of ribs 870 radiating in a generally sunburst pattern from a central port 880. Adjacent the central port 880, gaps 890 create diffusion zones for purge fluid coming out of the central port 880. The gaps 890 and the radiating ribs 870 cause the purge fluid to be distributed outward from the central port 880, causing a more uniform, improved regeneration of the adsorbent material during a purging step. The radiating ribs 870 also help to channel product gas towards the central port 880 during a product delivery step. In an alternative embodiment, the media retention cap 800 may have a generally non-cylindrical surface to retain media in a generally non-cylindrical adsorbtion bed 300. In a further alternative embodiment, the central port 880 may be located away from the geometric center of the either cylindrical or non-cylindrical media retention cap 800.

Figure 11A:
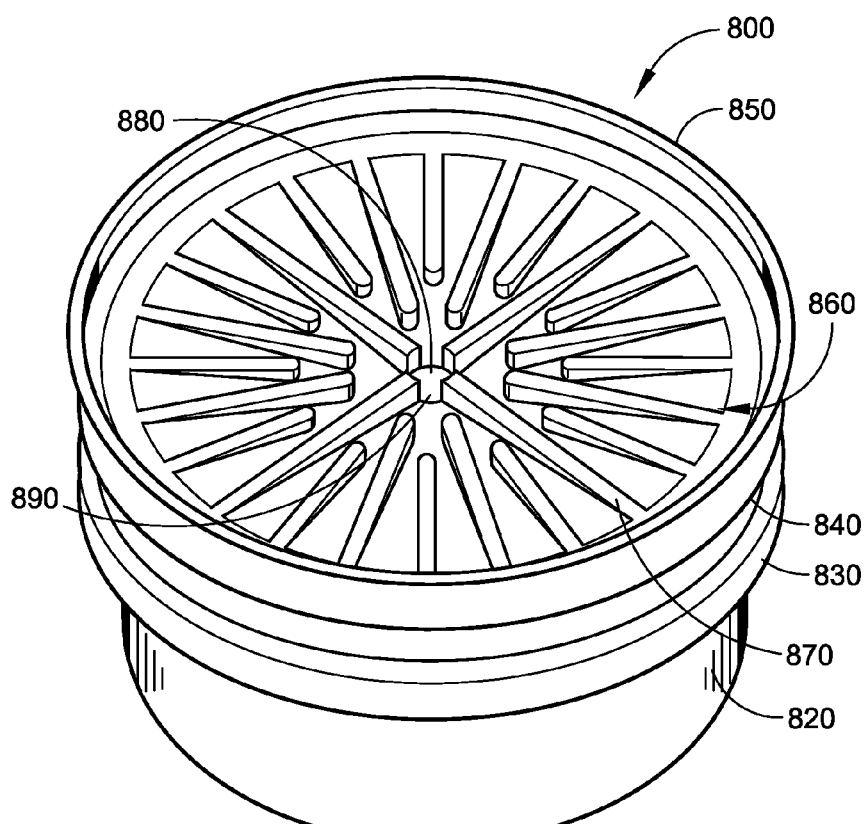
FIGS. 11A and 11B are a top perspective view and a bottom perspective view respectively of an embodiment of a media retention cap that may be used with the concentrator illustrated in FIGS. 7A and 7B.
Figure 11B:
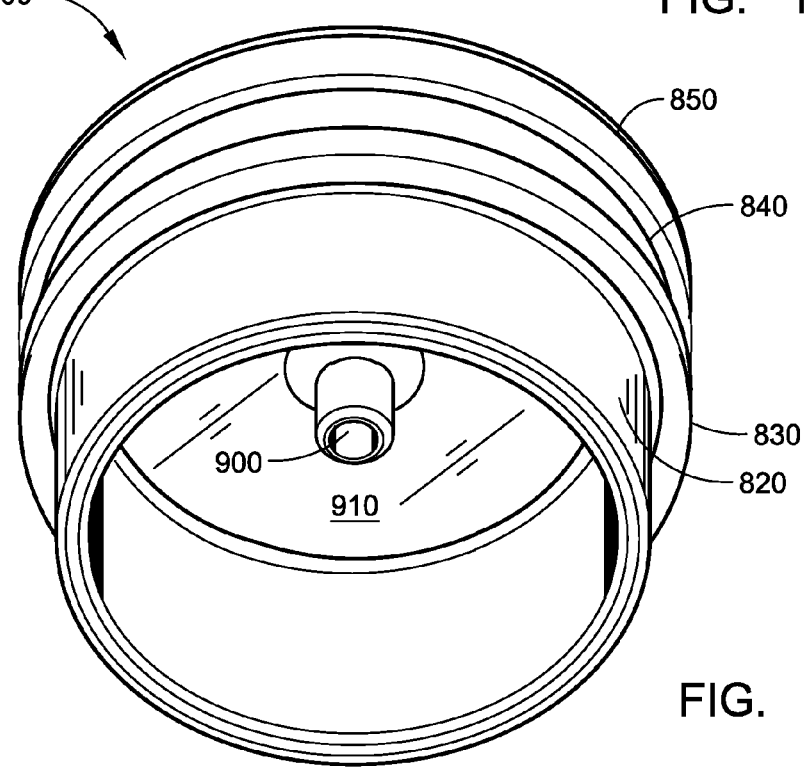

With reference to FIG. 11B, on the underside of the media retention cap 800, the cydrical base 820 forms an interior chamber in which the spring 810 is disposed. A central port nipple 900 extends from a bottom surface 910 of the media retention cap 800. An end of the product line 380 connects to the central port nipple 900 for communicating the product end 350 of the adsorption bed 300 with the incoming product passage 370 of the manifold 320.

In the past, media retention caps may be held in place with a spring that fits inside and above the cap so that the spring is in the fluid flow path between the bottom of the adsorbent material and any exit port, at the product end 350 of the bed 300. The volume in which the spring is housed represents dead volume in the system. As used herein, "dead volume" is system volume that is compressed and purged, but does not contain adsorbent media. The process of filling this volume with compressed feed and then venting that volume represents wasted feed. The improved media retention cap 800 does not add dead volume to the system because the spring 810 is housed outside of the fluid flow path. Elimination of any extra volume within the system results directly in more effective utilization of the feed, and, thus, higher recovery of the desired product.

With reference to FIGS. 12A and 12B, an embodiment of a centering mechanism for maintaining the rotary valve shoe 500 laterally fixed and centered with respect to the valve port plate 510 will now be described. The centering mechanism may include a centering pin 920 having a hollow cylindrical shape and made of a rigid material. When the engagement surface 520 of the rotary valve shoe 500 is engaged with the engagement surface 700 of the valve port plate 510, the centering pin 920 is partially disposed in the central feed pasage 600 of the rotary valve shoe 500 and the central incoming feed port 770 of the valve port plate 510. In use, the rotary valve shoe 500 rotates around the centering pin 920 and the hollow interior of the centering pin 920 allows high-pressure feed fluid to flow therethrough. The pin 920 maintains the rotating valve shoe in a fixed position relative to the valve port plate 510. In the past, the rotary valve shoe was roughly centered with respect to the valve port plate by the motor that drives the rotary valve shoe. If the rotary valve shoe 500 and the valve port plate 510 are off center with respect to each other, the concentrator 114 will not cycle as intended, inhibiting the productivity, recovery, and efficiency of the concentrator. The precision offered by the centering pin 920 is important when the valve assembly 310 is controlling complex cycles or maintaining very small pressure drops.

Figure 13A:
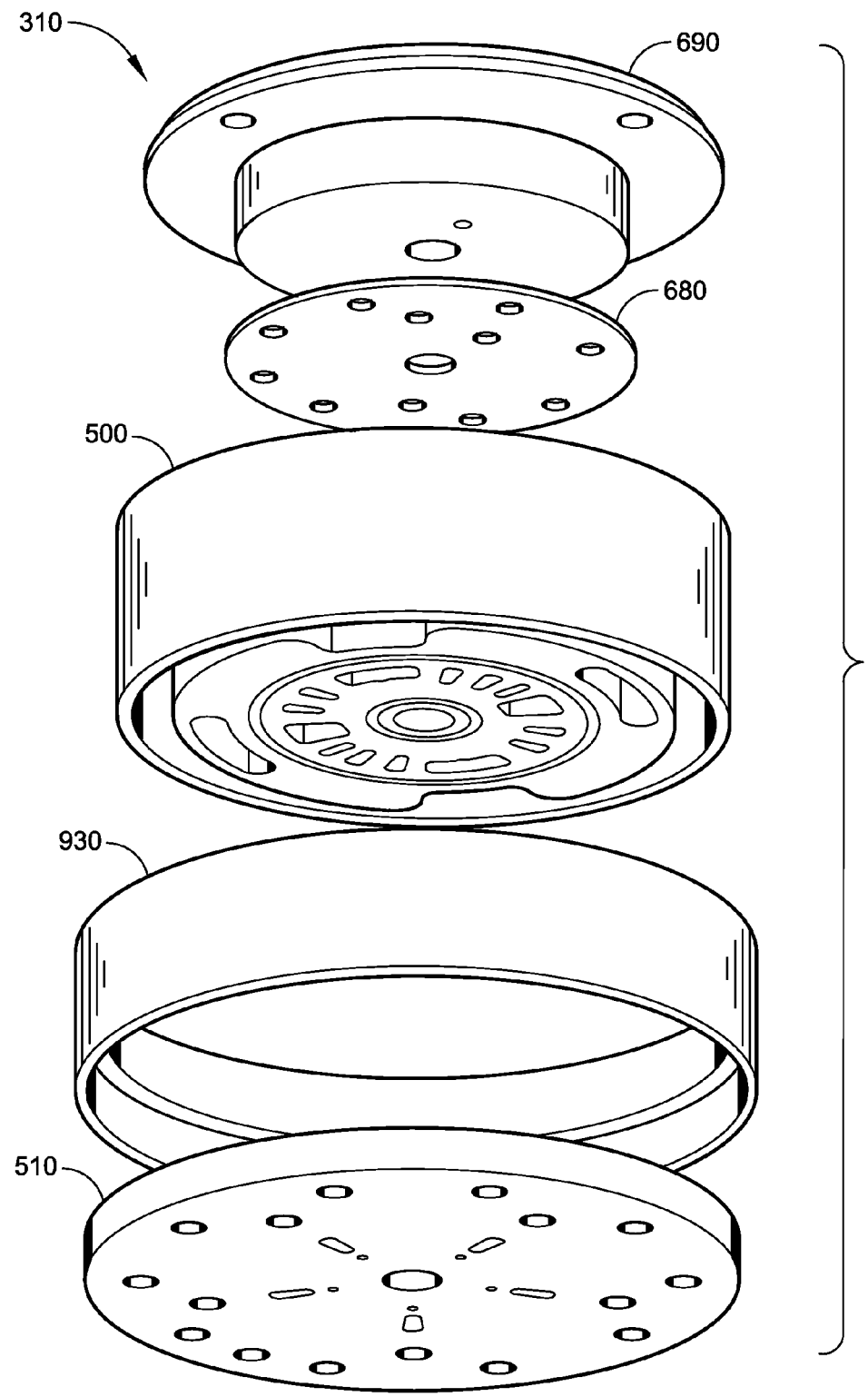
FIGS. 13A and 13B are a bottom perspective, exploded view and a top perspective, exploded view respectively of an embodiment of a rotary valve assembly including a centering ring that may be used with the concentrator illustrated in FIGS. 7A and 7B.
Figure 13B:
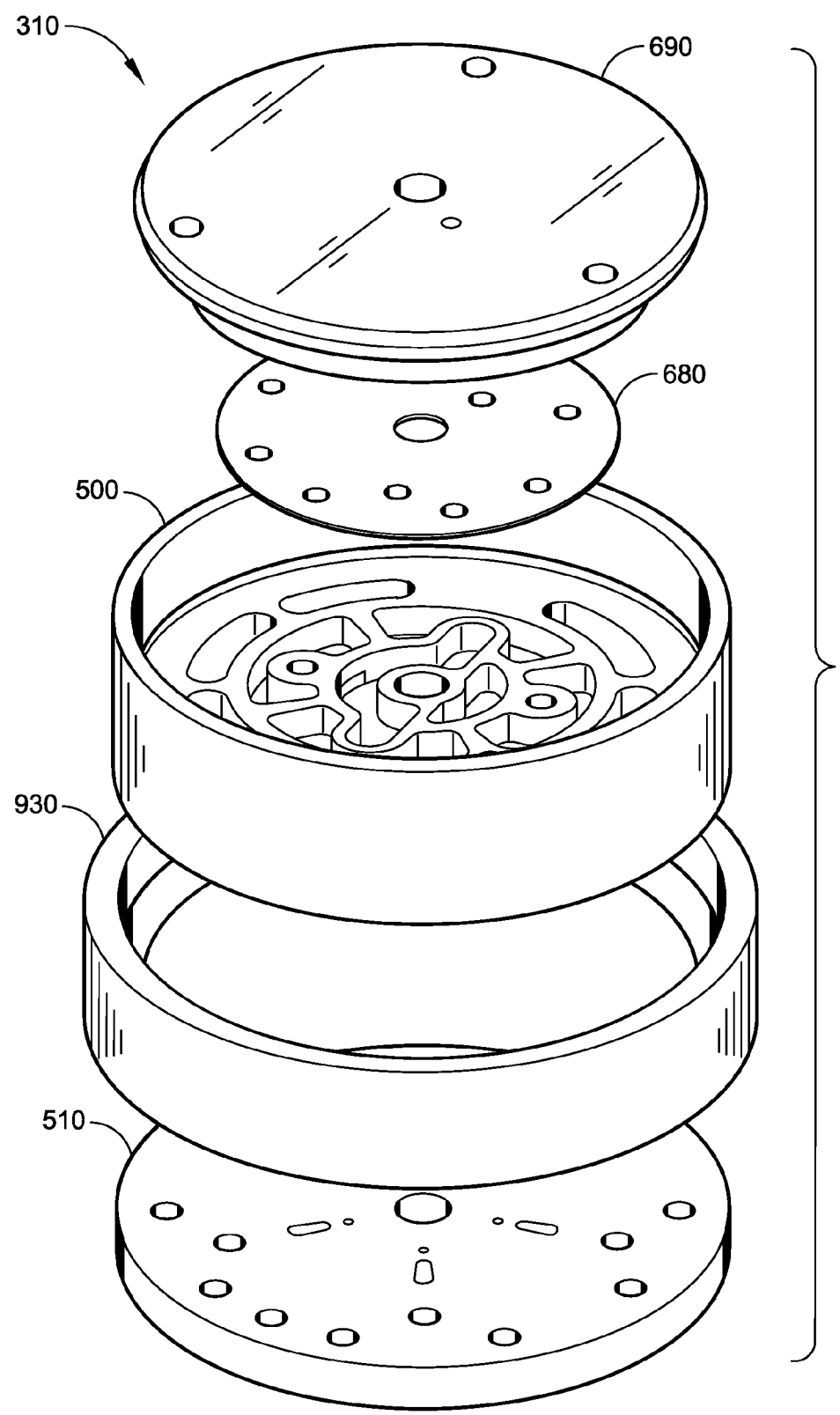

With reference to FIGS. 13A and 13B, a rotary valve assembly constructed in accordance with another embodiment of the invention includes an alternative centering mechanism to maintain the rotating valve shoe 500 in a fixed position relative to the valve port plate 510. A circular centering ring 930 fits snugly over the smooth cylindrical sidewall 530 of the rotary valve shoe 500 and the smooth cylindrical sidewall 710 of the stationary valve port plate 510. The circular ring 930 centers the rotary valve shoe 500 relative to the valve port plate 510 by holding the rotary shoe 500 in a fixed position relative to the port plate 510 while at the same time allowing the rotary valve shoe 500 to rotate.

Figure 14A:
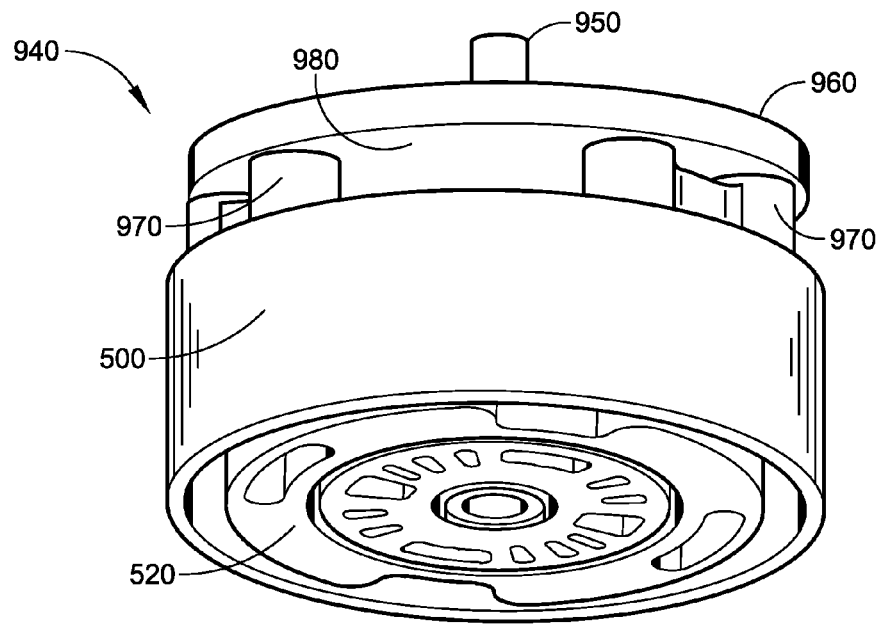
FIG. 14A is a bottom perspective view of an embodiment of a rotary valve shoe, a motor drive, and a pair of elastic chain links that may be used with the concentrator illustrated in FIGS. 7A and 7B.
Figure 14B:
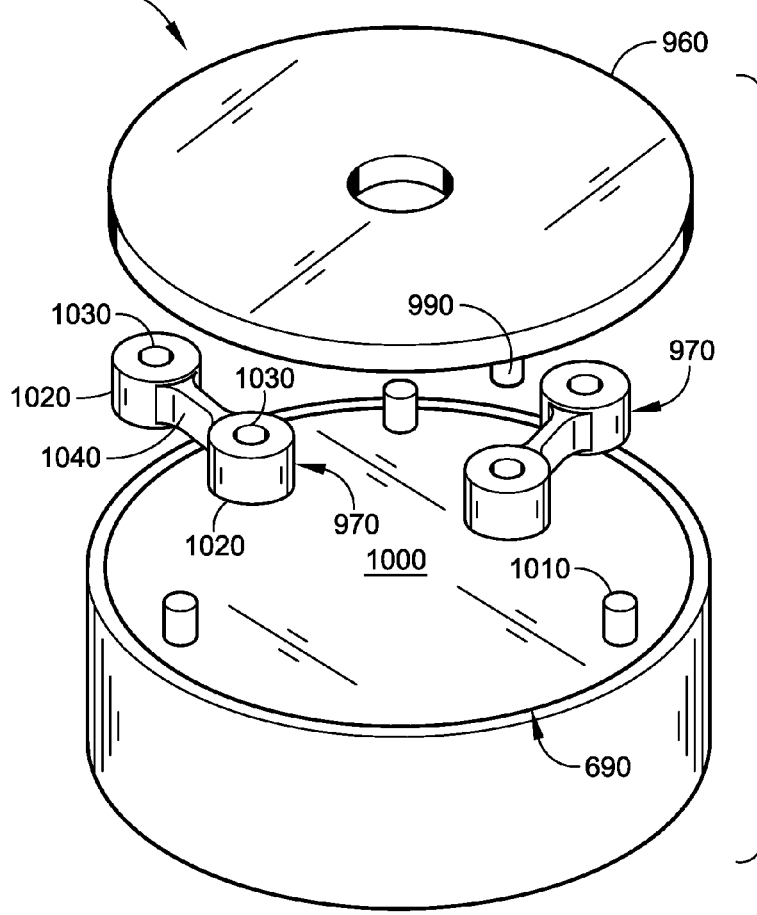
FIGS. 14B and 14C are a top perspective, exploded view and a bottom perspective, exploded view respectively of the rotary valve shoe, motor drive, and pair of elastic chain links illustrated in FIG. 14A.
Figure 14C:
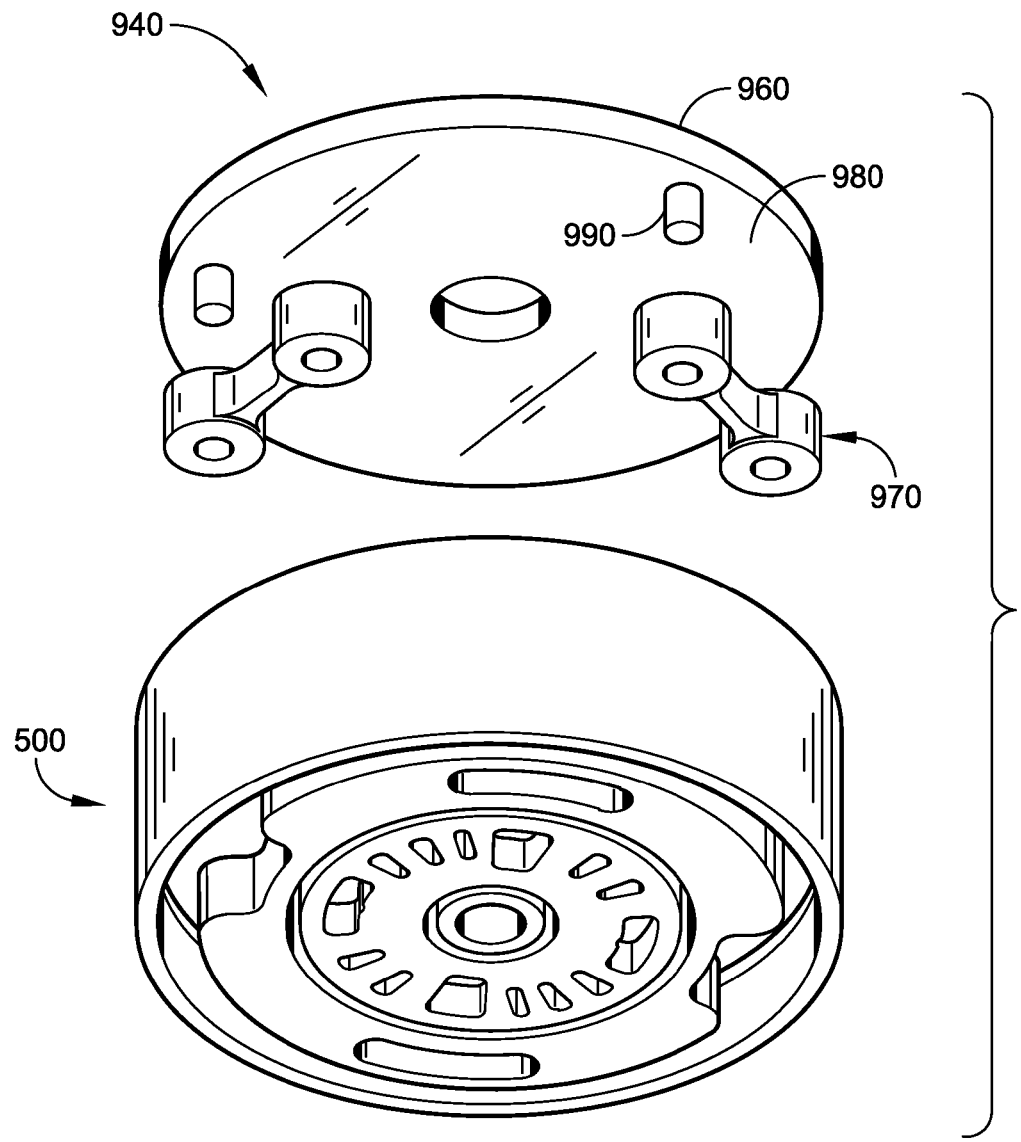
Figure 16:
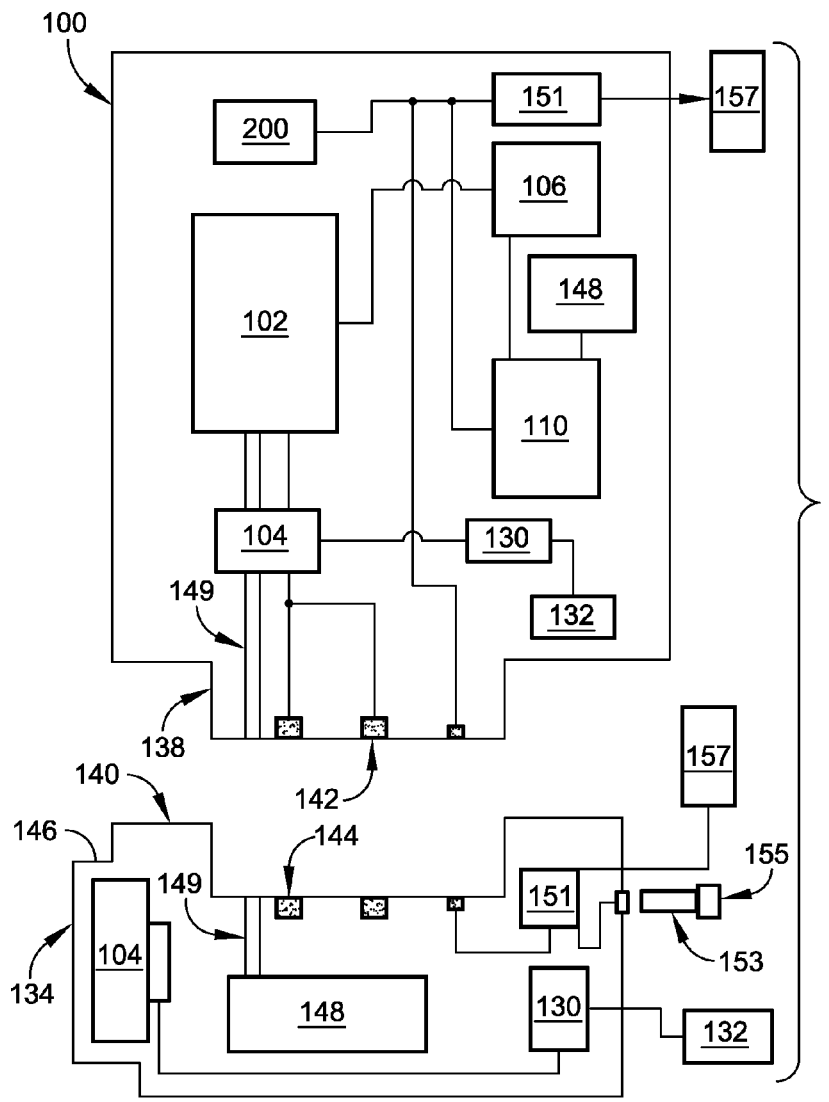
FIG. 16 is a schematic illustration of a further embodiment of the portable oxygen concentration system and an embodiment of a cradle for use with the portable oxygen concentration system.

With reference to FIGS. 14A-14C, an embodiment of an elastic link for coupling the motor 118 to the valve shoe 500 will now be described. A drive mechanism 940 includes a drive shaft 950, a drive wheel 960, and three (two shown) elastic chain links 970. The drive shaft 950 may be connected to the motor 118 for rotating the drive wheel 960. With reference to FIG. 14C, a lower side 980 of the drive wheel 960 may include downwardly protruding cylindrical support posts 990. Similarly, with reference to FIG. 14B, an upper side 1000 of the second valve shoe cover 690 may include upwardly protruding cylindrical support posts 1010. The elastic chain links 970 are preferably made of semi-rigid, elastic material (such as silicon rubber) and have a generally wrench-shaped configuration. Each elastic chain link 970 includes cylindrical receiving members 1020 with central cylindrical bores 1030. The cylindrical receiving members 1020 are joined by a narrow connecting member 1040. The drive wheel 960 is coupled to the second valve shoe cover 690 through the elastic chain links 970. One receiving member 1020 of each elastic chain link receives the support post 990 of the drive wheel 960 and the other receiving member 1020 receives the support post 1010 of the second valve shoe cover 690. In the past, rigid connections were made between the motor and the rotating valve shoe. These rigid connections caused the rotating valve shoe to be affected by vibration or other non-rotational movement of the motor. The elastic chain links 970 absorb the vibration and non-rotational movement of the motor, preventing this detrimental energy from being imparted to the rotating valve shoe 500.

FIG. 15 is a table of experimental data from a concentrator similar to the concentrator 114 shown and described above with respect to FIGS. 7-14. As shown by this table, the recovery of oxygen from air with the concentrator 114 is 45-71% at about 90% purity. The ratio of adiabatic power (Watts) to oxygen flow (Liters Per Minute) is in the range of 6.2 W/LPM to 23.0 W/LPM. As defined in Marks' Standard Handbook for Mechanical Engineers, Ninth Edition, by Eugene A. Avallone and Theodore Baumeister, the equation for adiabatic power, tanken from the equation from adiabatic work, is as follows:

$$\text{Power} = \frac{W}{t} = P_1 V_1 \left(\frac{k}{1-k}\right)\left[\left(\frac{P_2}{P_1}\right)^{\frac{k-1}{k}} - 1\right] C$$

Power=Adiabatic Power (Watts)
W=Adiabatic Work (Joule)
t=time (Second)
$P_1$=Atmospheric Pressure (psia)
$P_2$=Compressor/Vacuum pressure (psia)
k=Ratio of Specific Heats=constant=1.4 (for air)
$V_1$=Volumetric flow rate at atmospheric pressure (SLPM)
C=Conversion Factor, added by authors for clarity=0.114871 Watts/psi/LPM B. Energy Source With reference additionally to FIG. 16, in order to properly function as a lightweight, portable system 100, the system 100 must be energized by a suitable rechargeable energy source. The energy source preferably includes a rechargeable battery 104 of the lithium-ion type. It will be readily apparent to those skilled in the art that the system 100 may be powered by a portable energy source other than a lithium-ion battery. For example, a rechargeable or renewable fuel cell may be used. Although the system is generally described as being powered by a rechargeable battery 104, the system 100 may be powered by multiple batteries. Thus, as used herein, the word "battery" includes one or more batteries. Further, the rechargeable battery 104 may be comprised of one or more internal and/or external batteries. The battery 104 or a battery module including the battery 104 is preferably removable from the system 100. The system 100 may use a standard internal battery, a low-cost battery, an extended-operation internal battery, and an external secondary battery in a clip-on module.

The system 100 may have a built-in adapter including battery charging circuitry 130 and one or more plugs 132 configured to allow the system 100 to be powered from a DC power source (e.g., car cigarette lighter adapter) and/or an AC power source (e.g., home or office 110 VAC wall socket) while the battery 104 is simultaneously being charged from the DC or AC power source. The adapter or charger could also be separate accessories. For example, the adapter may be a separate cigarette lighter adapter used to power the system 100 and/or charge the battery 104 in an automobile. A separate AC adapter may be used to convert the AC from an outlet to DC for use by the system 100 and/or charging the battery 104. Another example of an adapter may be an adapter used with wheel chair batteries or other carts.

Alternatively, or in addition, a battery-charging cradle 134 adapted to receive and support the system 100 may have an adapter including battery charging circuitry 130 and a plug 132 that also allow the system 100 to be powered while the battery 104 is simultaneously being charged from a DC and/or AC power source.

The system 100 and cradle 134 preferably include corresponding mating sections 138, 140 that allow the system 100 to be easily dropped into and onto the cradle 134 for docking the system 100 with the cradle 134. The mating sections 138, 140 may include corresponding electrical contacts 142, 144 for electrically connecting the system 100 to the cradle 134.

The cradle 134 may be used to recharge and/or power the system 100 in the home, office, automobile, etc. The cradle 134 may be considered part of the system 100 or as a separate accessory for the system 100. The cradle 134 may include one or more additional charging receptacles 146 coupled to the charging circuitry 130 for charging spare battery packs 104. With a charging receptacle 146 and one or more additional battery packs 104, the user can always have a supply of additional fresh, charged batteries 104.

In alternative embodiments, the cradle 134 may come in one or more different sizes to accommodate one or more different types of systems 100.

The cradle 134 and/or system 100 may also include a humidifying mechanism 148 for adding moisture to the air flow in the system 100 through appropriate connections 149. In an alternative embodiment of the invention, the humidifying mechanism 148 may be separate from the system 100 and the cradle 134. If separate from the system 100 and cradle 134, the cradle 134 and/or system 100 may include appropriate communication ports for communicating with the separate humidifying mechanism 148. The cradle 134 may also include a receptacle adapted to receive a separate humidifying mechanism 148 for use with the system 100 when the system 100 is docked at the cradle 134.

The cradle 134 and/or system 100 may also include a telemetry mechanism or modem 151 such as a telephone modem, high-speed cable modem, RF wireless modem or the like for communicating the control unit 110 of the system 100 with one or more remote computers. To this end, the cradle 135 may include a line 153 with a cable adapter or telephone jack plug 155, or a RF antenna 157. In an alternative embodiment of the invention, the telemetry mechanism or modem 151 may be separate from the cradle 134 and to this end, the cradle 134 or system 100 may include one or more appropriate communication ports, e.g., a PC port, for directly communicating the telemetry mechanism or modem 151 with the cradle 134 or system 100. For example, the cradle 134 may be adapted to communicate with a computer (at the location of the cradle) that includes the telemetry mechanism or modem 151. The computer may include appropriate software for communicating information described below using the telemetry mechanism or modem 151 with the one or more remote computers.

The telemetry mechanism or modem 151 may be used to communicate physiological information of the user such as, but not by way of limitation, heart rate, oxygen saturation, respiratory rate, blood pressure, EKG, body temperature, inspiratory/expiratory time ratio (I to E ratio) with one or more remote computers. The telemetry mechanism or modem 151 may be used to communicate other types of information such as, but not by way of limitation, oxygen usage, maintenance schedules on the system 100, and battery usage with one or more remote computers.

A user ideally uses the system 100 in its cradle 134 at home, at the office, in the automobile, etc. A user may decide to have more than one cradle, e.g., one at home, one at the office, one in the automobile, or multiple cradles at home, one in each room of choice. For example, if the user has multiple cradles 134 at home, when the user goes from room to room, e.g., from the family room to the bedroom, the user simply lifts the system 100 out of its cradle 134 in one room, and walks to the other room under battery operation. Dropping the system 100 in a different cradle 134 in th destination room restores the electrical connection between the system 100 and the AC power source. Since the system's batteries 104 are constantly charging or charged when located in the cradle 134, excursions outside the home, office, etc. are as simple as going from room to room in the user's home.

Because the system 100 is small and light, the system 100 may simply be lifted from the cradle 134 and readily carried, e.g., with a shoulder strap, by an average user to the destination. If the user is unable to carry the system 100, the system 100 may be readily transported to the destination using a cart or other transporting apparatus. For an extended time away from home, office, etc., the user may bring one or more cradles 134 for use at the destination. Alternatively, in the embodiment of the system 100 including the built-in adapter, power may be drawn from power sources such as a car cigarette lighter adapter and/or an AC power outlet available at the destination. Further, spare battery Packs 104 may be used for extended periods away from standard power sources.

If the battery pack 104 includes multiple batteries, the system 100 may include a battery sequencing mechanism to conserve battery life as is well known in the cellphone and laptop computer arts.

C. Output Sensor

Figure 17:
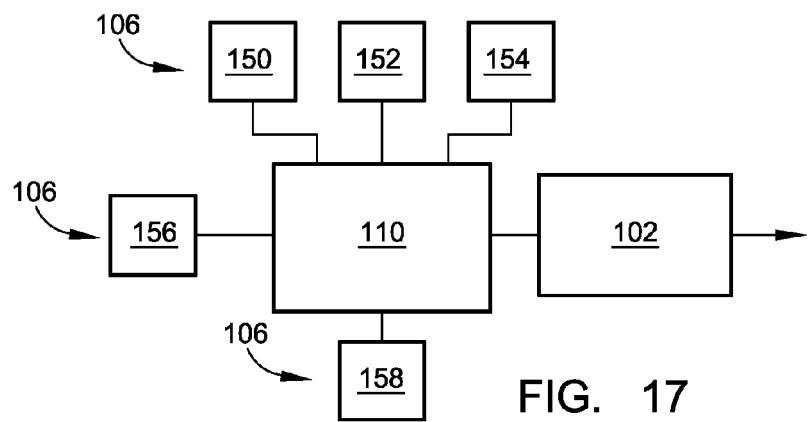
FIG. 17 is a block diagram of the one or more sensors that may be used with an embodiment of the portable oxygen concentration system.

With reference to FIGS. 5, 6 and 17, one or more output sensors 106 are used to sense one or more conditions of the user 108, environment, etc. to determine the oxygen flow rate needs of the user and, hence, the oxygen flow rate output requirements for the system 100. A control unit 110 is linked to the one or more output sensors 106 and the oxygen gas generator 102 to control the oxygen generator 102 in response to the condition(s) sensed by the one or more output sensors 106. For example, but not by way of limitation, the output sensor(s) 106 may include at least one of, but not by way of limitation, a pressure sensor 150, a position sensor 152, an acceleration sensor 154, a physiological condition or metabolic sensor 156, and/or an altitude sensor 158.

The first three sensors 150, 152, 154 (and, in certain circumstances, the physiological condition sensor 156) are activity sensors because these sensors provide a signal representing activity of the user 108. In the delivery of oxygen with a portable oxygen concentration system, it is important to deliver an amount of oxygen gas proportional to the activity level of the user 108 without delivering too much oxygen. Too much oxygen may be harmful for the user 108 and reduces the life of the battery 104. The control unit 110 regulates the oxygen gas generator 102 to control the flow rate of oxygen gas to the user 108 based on the one or more signals representative of the activity level of the user produced by the one or more sensors 106. For example, if the output sensor(s) 106 indicates that the user 108 has gone from an inactive state to an active state, the control unit 110 may cause the oxygen gas generator 102 to increase the flow rate of oxygen gas to the user 108 and/or may provide a burst of oxygen gas to the user 108 from a high-pressure oxygen reservoir to be described. If the output sensor(s) 106 indicates that the user 108 has gone from an active state to an inactive state, the control unit 110 may cause the oxygen gas generator 102 to reduce the flow rate of oxygen gas to the user.

In an embodiment of the invention, the amount of oxygen gas supplied is controlled by controlling the speed of the compressor motor 118 via the variable-speed controller 119.

Alternatively, or in addition to the variable-speed controller, the supply of oxygen gas may be controlled by the supply valve 160 located in the supply line 121 between the oxygen gas (generator 102 and the user 108. For example, the supply valve 160 may be movable between at least a first position and a second position, the second position allowing a greater flow of concentrated gaseous oxygen through than the first position. The control unit 110 may cause the supply valve 160 to move from the first position to the second position when one or more of the activity level sensors 152, 154, 156 senses an active level of activity of the user 108. For example, the control unit 110 may include a timer, and when an active level is sensed for a time period exceeding a predetermined timed period, the control unit 110 causes the valve 160 to move from the first position to the second position.

Examples of pressure sensors 150 include, without limitation, a foot switch that indicates when a user is in a standing position compared to a sedentary position, and a seat switch that indicates when a user is in a seated position compared to a standing position.

A pendulum switch is an example of a position sensor 152. For example, a pendulum switch may include a thigh switch positioned pendulously to indicate one mode when the user is standing, i.e., the switch hangs vertically, and another mode when the user seated, i.e., the thigh switch raised to a more horizontal position. A mercury switch may be used as a position sensor.

An acceleration sensor 158 such as an accelerometer is another example of an activity sensor that provides a signal representing activity of the user.

The physiological condition or metabolic sensor 156 may also function as an activity sensor. The physiological condition sensor 156 may be used to monitor one or more physiological conditions of the user for controlling the oxygen gas generator 102 or for other purposes. Examples of physiological conditions that may be monitored with the sensor 156 include, but without limitation, blood oxygen level, heart rate, respiration rate, blood pressure, EKG, body temperature, and I to E ratio. An oximeter is an example of a sensor that is preferably used in the system 100. The oximeter measures the blood oxygen level of the user, upon which oxygen production may be at least partially based.

An altitude sensor 158 is an example of an environmental or ambient condition sensor that may sense an environmental or ambient condition upon which control of the supply of oxygen gas to the user may be at least partially based. The altitude sensor 158 may be used alone or in conjunction with any or all of the above sensors, the control unit 110 and the oxygen gas generator 102 to control the supply of oxygen gas to the user in accordance with the sensed altitude or elevation. For example, at higher sensed elevations, where air is less concentrated, the control unit may increase the flow rate of oxygen gas to the user 108 and at lower sensed elevations, where air is more concentrated, the control unit may decrease the flow rate of oxygen gas to the user 108 or maintain it at a control level.

It will be readily apparent to those skilled in the art that one or more additional or different sensors may be used to sense a condition upon which control of the supply of oxygen gas to the user may be at least partially based. Further, any or all of the embodiments described above for regulating the amount of oxygen gas supplied to the user 108, i.e., variable-speed controller 119, supply valve 160, (or alternative embodiments) may be used with the one or more sensors and the control unit 110 to control of the supply of oxygen gas to the user 108.

D. Control Unit

Figure 18:
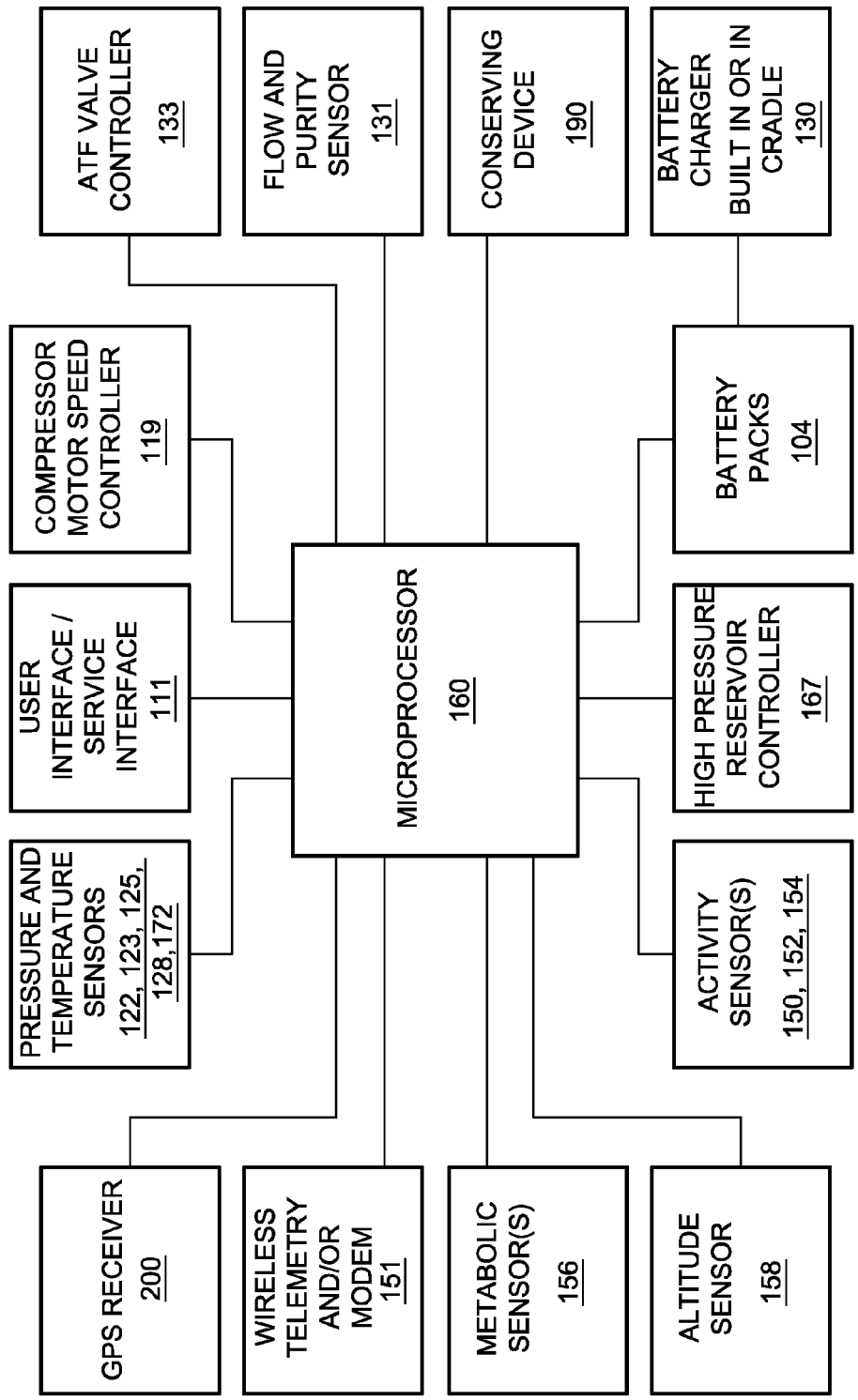
FIG. 18 is a block diagram of the one or more components that may be controlled by the control unit of the portable oxygen concentration system.

With reference to FIG. 18, the control unit 110 may take any well-known form in the art and includes a central microprocessor or CPU 160 in communication with the components of the system described herein via one or more interfaces, controllers, or other electrical circuit elements for controlling and managing the system. The system 100 may include a user interface (FIG. 18) as part of the control unit 110 or coupled to the control unit 110 for allowing the user, provider, doctor, etc. to enter information, e.g., prescription oxygen level, flow rate, activity level, etc., to control the system 100.

The main elements of an embodiment of the system 100 have been described above. The following sections describe a number of additional features, one or more of which may be incorporated into the embodiments of the invention described above as one or more separate embodiments of the invention.

II. Conserving Device

Figure 19:
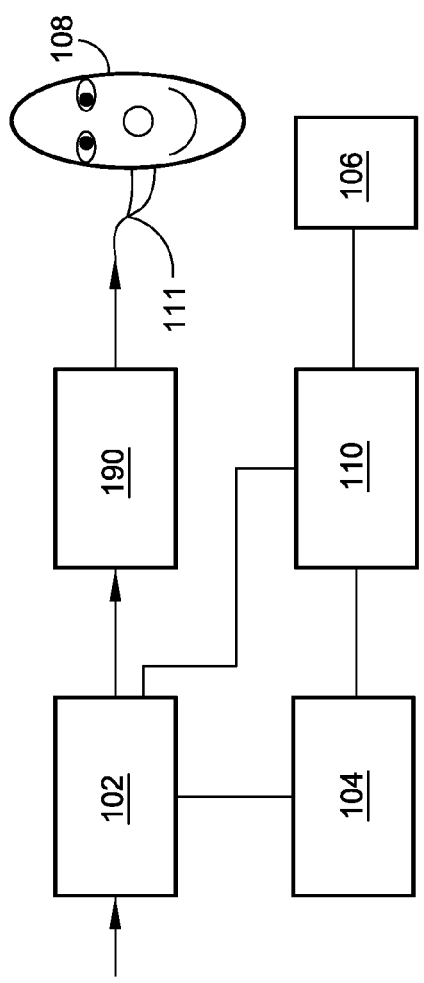
FIG. 19 is a block diagram of a portable oxygen concentration system constructed in accordance with additional embodiment of the invention.

With reference to FIG. 19, a conserving device or demand device 190 may be incorporated into the system 100 to more efficiently utilize the oxygen produced by the oxygen gas generator 102. During normal respiration, a user 108 inhales for about one-third of the time of the inhale/exhale cycle and exhales the other two-thirds of the time. Any oxygen flow provided to the user 108 during exhalation is of no use to the user 108 and, consequently, the additional battery power used to effectively provide this extra oxygen flow is wasted. A conserving device 190 may include a sensor that senses the inhale/exhale cycle by sensing pressure changes in the cannula 111 or another part of the system 100, and supply oxygen only during the inhale portion or a fraction of the inhale portion of the breathing cycle. For example, because the last bit of air inhaled is of no particular use because it is trapped between the nose and the top of the lungs, the conserving device 190 may be configured to stop oxygen flow prior to the end of inhalation, improving the efficiency of the system 100. Improved efficiency translates into a reduction in the 20 size, weight, cost and power requirements of the system 100.

The conserving device 190 may be a stand-alone device in the output line of the system 100, similar to a regulator for scuba diving, or may be coupled to the control unit 110 for controlling the oxygen generator 102 to supply oxygen only during inhalation by the user 108.

The conserving device 190 may include one or more of the sensors described above. For example, the conserving device may include a sensor for monitoring the respiration rate of the user.

The system 100 may also include a special cannula retraction device for retracting the cannula ill when not in use. Further, the cannula 111 may come in different lengths and sizes.

III. High-Pressure Reservoir

Figure 20:
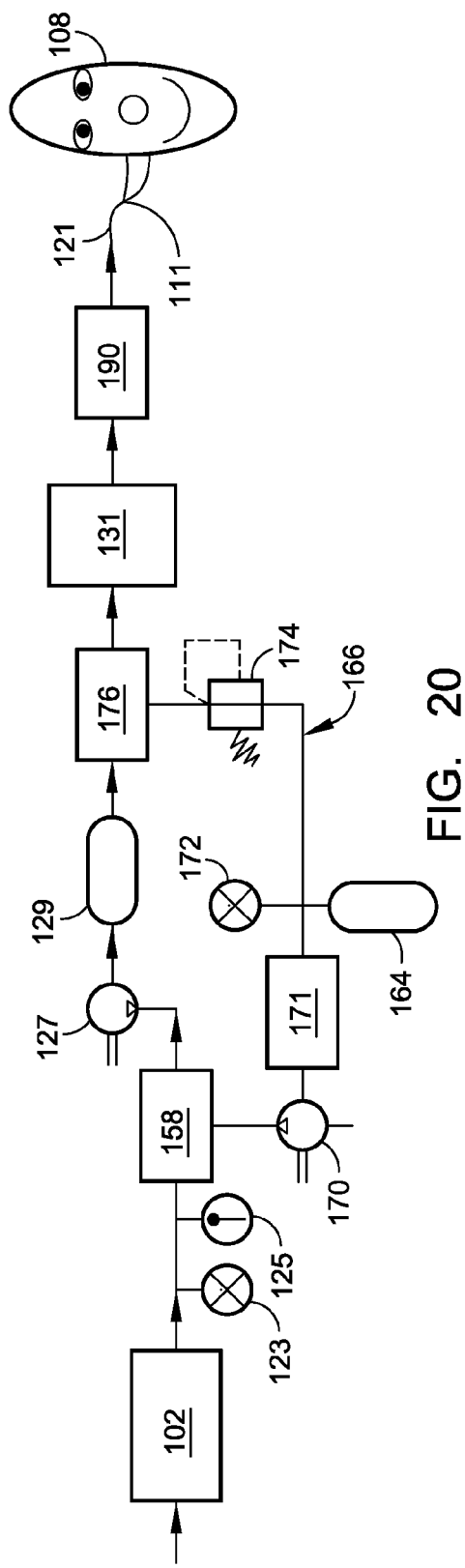
FIG. 20 is a schematic illustration of another embodiment of a portable oxygen concentration system including a high-pressure reservoir.

With reference to FIG. 20, a high-pressure reservoir 164 may be located in a secondary line 166 for delivering an additional supply of oxygen gas to the user 108 when the oxygen gas generator 102 can not meet the oxygen gas demands of the user 108. Any of the components described below in the secondary line 166 may be coupled to the control unit 110 or a high-pressure reservoir controller 167 (FIG. 18) for control thereby. Exemplary situations where this additional oxygen gas need may occur are when a user suddenly goes from an inactive state to an active state, e.g., when getting out of a chair, when the system 100 is turned on, or when the system 100 goes from a conserving mode or sleep mode to an active mode. As used herein, secondary line 166 refers to the tubing, connectors, etc. used to connect the components in the line. A valve 168 may be controlled by the control unit 110 to allow gaseous oxygen to flow into the secondary line 166. The valve 168 may be configured to allow simultaneous flow to both the supply line 121 and the secondary line 166, flow to only the supply line 121, or flow to only the secondary line 166.

A pump or compressor 168, which is preferably powered by the motor 118, delivers the oxygen gas at a relatively high pressure, e.g., at least approximately 100 psi, to the high-pressure reservoir 164.

An oxygen-producing electrochemical cell 171 may be used in conjunction with or instead of the elements described in the secondary line 166 to supply additional oxygen gas to the user 108. For example the electrochemical cell 171 may be used to deliver oxygen gas at a relatively high pressure to the highpressure reservoir 164.

A pressure sensor 172 is in communication with the high-pressure reservoir 164 and the control unit 110 so that when the pressure in the high-pressure reservoir 164 reaches a certain limit, the control unit 110 causes the valve 168 to direct oxygen to the secondary line 166.

A regulator 174 may be used to control flow and reduce pressure of the oxygen gas to the user 108.

A valve 176 may also be controlled by the control unit 110 to allow gaseous oxygen from the high-pressure reservoir 164 to flow into the supply line 121 when the user 108 requires an amount of oxygen gas that cannot be met by the oxygen gas generator 102. The valve 176 may be configured to allow simultaneous flow from the oxygen gas generator 102 and the high-pressure reservoir 164, from only the oxygen gas generator 102, or from only the high-pressure reservoir 164.

The one or more sensors 106 are interrelated with the control unit 110 and the oxygen gas generator 102 so as to supply an amount of oxygen gas equivalent to the oxygen gas needs of the user 108 based at least in part upon one or more conditions sensed by the one or more sensors 106. When the oxygen gas generator 102 cannot meet the oxygen gas demands of the user 108, the control unit 110, based at least in part upon sensing one or more conditions indicative of the oxygen needs of the user, may cause the high-pressure reservoir 164 (via the valve 176) to supply the additional oxygen gas needed.

In the scenario where the oxygen gas generator 102 is capable of supplying the full oxygen gas needs of the user 108, but is simply turned off or is in a conserving or sleep mode, the period of time that the high-pressure reservoir 164 supplies the oxygen gas, i.e., the period of time that the valve 176 connects the high-pressure reservoir 164 with the supply line 121, is at least as long as the time required for the oxygen gas generator 102 to go from an off or inactive condition to an on or active condition. In another scenario, the control unit 110 may cause oxygen gas to be supplied to the user from the high-pressure reservoir 164 when the demand for gaseous oxygen by the user exceeds the maximum oxygen gas output of the oxygen gas generator 102. Although the high-pressure reservoir 164 is shown and described as being filled by the oxygen gas generator 102, in an alternative embodiment, the high-pressure reservoir 164 may be filled by a source outside or external to the system.

IV. Global Positioning System

With reference back to FIG. 16, in an alternative embodiment of the invention, the system 100 may include a global positioning system (GPS) receiver 200 for determining the location of the system 100. The location of the receiver 200 and, hence, the user 108 can be transmitted to a remote computer via the telemetry mechanism or modem 151. This may be desirable for locating the user 108 in the event the user has a health problem, e.g., heart attack, hits a panic button on the system, an alarm is actuated on the system, or for some other reason.

V. Additional Options and Accessories

In addition to the cradle 134, the portable oxygen concentration system 100 may include additional options and accessories. A number of different types of bags and carrying cases such as, but not by way of limitation, a shoulder bag, a backpack, a fanny pack, a front pack, and a split pack in different colors and patterns may be used to transport the system 100 or other system accessories. A cover may be used to shield the system from inclement weather or other environmental damage. The system 100 may also be transported with a rolling trolley/cart, a suit case, or a travel case. The travel case may be designed to carry the system 100 and include enough room to carry the cannulae 111, extra batteries, an adapter, etc. Examples of hooks, straps, holders for holding the system 100 include, but not by way of limitation, hooks for seatbelts in cars, hooks/straps for walkers, hooks/straps, for wheel chairs, hooks/straps for hospital beds, hooks for other medical devices such as ventilators, hooks/straps for a golf bag or golf cart, hooks/straps for a bicycle, and a hanging hook. The system 100 may also include one or more alarm options. An alarm of the system 100 may be actuated if, for example, a sensed physiological condition of the user 108 falls outside a pre-defined range. Further, the alarm may include a panic alarm that may be manually actuated by the user 108. The alarm may actuate a buzzer or other sounding device on the system 100 and/or cause a communication to be sent via the telemetry mechanism or modem 151 to another entity, e.g., a doctor, a 911 dispatcher, a caregiver, a family member, etc.

Figure 21:
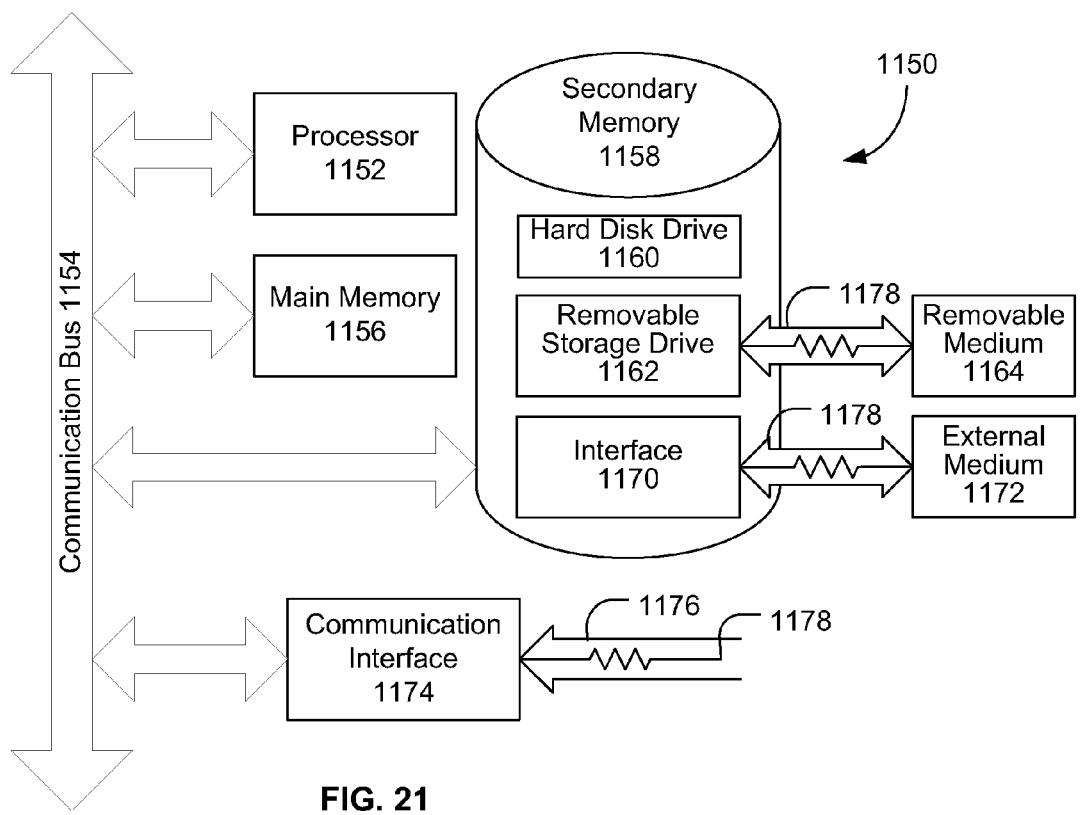
FIG. 21 is a block diagram illustrating an example computer system that may be used in connection with various embodiments described herein.

FIG. 21 is a block diagram illustrating an example computer system 1150 that may be used in connection with the embodiment of the control units and/or computers described herein. However, other computer systems and/or architectures may be used, as will be clear to those skilled in the art.

The computer system 1150 preferably includes one or more processors, such as processor 1152. Additional processors may be provided, such as an auxiliary processor to manage input/output, an auxiliary processor to perform floating point mathematical operations, a special-purpose microprocessor having an architecture suitable for fast execution of signal processing algorithms (e.g., digital signal processor), a slave processor subordinate to the main processing system (e.g., back-end processor), an additional microprocessor or controller for dual or multiple processor systems, or a coprocessor. Such auxiliary processors may be discrete processors or may be integrated with the processor 1152.

The processor 1152 is preferably connected to a communication bus 1154. The communication bus 1154 may include a data channel for facilitating information transfer between storage and other peripheral components of the computer system 1150. The communication bus 1154 further may provide a set of signals used for communication with the processor 1152, including a data bus, address bus, and control bus (not shown). The communication bus 1154 may comprise any standard or non-standard bus architecture such as, for example, bus architectures compliant with industry standard architecture ("ISA"), extended industry standard architecture ("EISA"), Micro Channel Architecture ("MCA"), peripheral component interconnect ("PCI") local bus, or standards promulgated by the Institute of Electrical and Electronics Engineers ("IEEE") including IEEE 488 general-purpose interface bus ("GPIB"), IEEE 696/S-100, and the like.

Computer system 1150 preferably includes a main memory 1156 and may also include a secondary memory 1158. The main memory 1156 provides storage of instructions and data for programs executing on the processor 1152. The main memory 1156 is typically semiconductor-based memory such as dynamic random access memory ("DRAM") and/or static random access memory ("SRAM"). Other semiconductor-based memory types include, for example, synchronous dynamic random access memory ("SDRAM"), Rambus dynamic random access memory ("RDRAM"), ferroelectric random access memory ("FRAM"), and the like, including read only memory ("ROM").

The secondary memory 1158 may optionally include a hard disk drive 1160 and/or a removable storage drive 1162, for example a floppy disk drive, a magnetic tape drive, a compact disc ("CD") drive, a digital versatile disc ("DVD") drive, etc. The removable storage drive 1162 reads from and/or writes to a removable storage medium 1164 in a well-known manner. Removable storage medium 1164 may be, for example, a floppy disk, magnetic tape, CD, DVD, etc.

The removable storage medium 1164 is preferably a computer readable medium having stored thereon computer executable code (i.e., software) and/or data. The computer software or data stored on the removable storage medium 1164 is read into the computer system 1150 as electrical communication signals 1178.

In alternative embodiments, secondary memory 1158 may include other similar means for allowing computer programs or other data or instructions to be loaded into the computer system 1150. Such means may include, for example, an external storage medium 1172 and an interface 1170. Examples of external storage medium 1172 may include an external hard disk drive or an external optical drive, or and external magneto-optical drive.

Other examples of secondary memory 1158 may include semiconductor-based memory such as programmable read-only memory ("PROM"), erasable programmable read-only memory ("EPROM"), electrically erasable read-only memory ("EEPROM"), or flash memory (block oriented memory similar to EEPROM). Also included are any other removable storage units 1172 and interfaces 1170, which allow software and data to be transferred from the removable storage unit 1172 to the computer system 1150.

Computer system 1150 may also include a communication interface 1174. The communication interface 1174 allows software and data to be transferred between computer system 1150 and external devices (e.g. printers), networks, or information sources. For example, computer software or executable code may be transferred to computer system 1150 from a network server via communication interface 1174. Examples of communication interface 1174 include a modem, a network interface card ("NIC"), a communications port, a PCMCIA slot and card, an infrared interface, and an IEEE 1394 fire-wire, just to name a few.

Communication interface 1174 preferably implements industry promulgated protocol standards, such as Ethernet IEEE 802 standards, Fiber Channel, digital subscriber line ("DSL"), asynchronous digital subscriber line ("ADSL"), frame relay, asynchronous transfer mode ("ATM"), integrated digital services network ("ISDN"), personal communications services ("PCS"), transmission control protocol/Internet protocol ("TCP/IP"), serial line Internet protocol/point to point protocol ("SLIP/PPP"), and so on, but may also implement customized or non-standard interface protocols as well.

Software and data transferred via communication interface 1174 are generally in the form of electrical communication signals 1178. These signals 1178 are preferably provided to communication interface 1174 via a communication channel 1176. Communication channel 1176 carries signals 1178 and can be implemented using a variety of wired or wireless communication means including wire or cable, fiber optics, conventional phone line, cellular phone link, wireless data communication link, radio frequency (RF) link, or infrared link, just to name a few.

Computer executable code (i.e., computer programs or software) is stored in the main memory 1156 and/or the secondary memory 1158. Computer programs can also be received via communication interface 1174 and stored in the main memory 1156 and/or the secondary memory 1158. Such computer programs, when executed, enable the computer system 1150 to perform the various functions of the present invention as previously described.

In this description, the term "computer readable medium" is used to refer to any media used to provide computer executable code (e.g., software and computer programs) to the computer system 1150. Examples of these media include main memory 1156, secondary memory 1158 (including hard disk drive 1160, removable storage medium 1164, and external storage medium 1172), and any peripheral device communicatively coupled with communication interface 1174 (including a network information server or other network device). These computer readable mediums are means for providing executable code, programming instructions, and software to the computer system 1150.

In an embodiment that is implemented using software, the software may be stored on a computer readable medium and loaded into computer system 1150 by way of removable storage drive 1162, interface 1170, or communication interface 1174. In such an embodiment, the software is loaded into the computer system 1150 in the form of electrical communication signals 1178. The software, when executed by the processor 1152, preferably causes the processor 1152 to perform the inventive features and functions previously described herein.

Various embodiments may also be implemented primarily in hardware using, for example, components such as application specific integrated circuits ("ASICs"), or field programmable gate arrays ("FPGAs"). Implementation of a hardware state machine capable of performing the functions described herein will also be apparent to those skilled in the relevant art. Various embodiments may also be implemented using a combination of both hardware and software.

Furthermore, those of skill in the art will appreciate that the various illustrative logical blocks, modules, circuits, and method steps described in connection with the above described figures and the embodiments disclosed herein can often be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled persons can implement the described functionality in varying ways for each particular application, but such implementation decisions should not be interpreted as causing a departure from the scope of the invention. In addition, the grouping of functions within a module, block, circuit or step is for ease of description. Specific functions or steps can be moved from one module, block or circuit to another without departing from the invention.

Moreover, the various illustrative logical blocks, modules, and methods described in connection with the embodiments disclosed herein can be implemented or performed with a general purpose processor, a digital signal processor ("DSP"), an ASIC, FPGA or other programmable logic device, discrete gate or transistor logic, discrete hardware components, or any combination thereof designed to perform the functions described herein. A general-purpose processor can be a microprocessor, but in the alternative, the processor can be any processor, controller, microcontroller, or state machine. A processor can also be implemented as a combination of computing devices, for example, a combination of a DSP and a microprocessor, a plurality of microprocessors, one or more microprocessors in conjunction with a DSP core, or any other such configuration.

Additionally, the steps of a method or algorithm described in connection with the embodiments disclosed herein can be embodied directly in hardware, in a software module executed by a processor, or in a combination of the two. A software module can reside in RAM memory, flash memory, ROM memory, EPROM memory, EEPROM memory, registers, hard disk, a removable disk, a CD-ROM, or any other form of storage medium including a network storage medium. An exemplary storage medium can be coupled to the processor such the processor can read information from, and write information to, the storage medium. In the alternative, the storage medium can be integral to the processor. The processor and the storage medium can also reside in an ASIC.

The above figures may depict exemplary configurations for the invention, which is done to aid in understanding the features and functionality that can be included in the invention. The invention is not restricted to the illustrated architectures or configurations, but can be implemented using a variety of alternative architectures and configurations. Additionally, although the invention is described above in terms of various exemplary embodiments and implementations, it should be understood that the various features and functionality described in one or more of the individual embodiments with which they are described, but instead can be applied, alone or in some combination, to one or more of the other embodiments of the invention, whether or not such embodiments are described and whether or not such features are presented as being a part of a described embodiment. Thus the breadth and scope of the present invention, especially in the following claims, should not be limited by any of the above-described exemplary embodiments.

Terms and phrases used in this document, and variations thereof, unless otherwise expressly stated, should be construed as open ended as opposed to limiting. As examples of the foregoing: the term "including" should be read as mean "including, without limitation" or the like; the term "example" is used to provide exemplary instances of the item in discussion, not an exhaustive or limiting list thereof; and adjectives such as "conventional," "traditional," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, a group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should also be read as "and/or" unless expressly stated otherwise. Furthermore, although item, elements or components of the disclosure may be described or claimed in the singular, the plural is contemplated to be within the scope thereof unless limitation to the singular is explicitly stated. The presence of broadening words and phrases such as "one or more," "at least," "but not limited to" or other like phrases in some instances shall not be read to mean that the narrower case is intended or required in instances where such broadening phrases may be absent.

We claim:

1. A method of titration using a combination continuous flow and pulse flow portable oxygen concentration system with a patient, comprising:
   a) providing the portable oxygen concentration system in a continuous flow mode and titrating the patient to a predetermined blood oxygen saturation using the portable oxygen concentration system at one or more predetermined conditions in the continuous flow mode;

b) providing the portable oxygen concentration system in a pulse flow mode and titrating the patient to the same predetermined blood oxygen saturation as step a using the portable oxygen concentration system at the same one or more predetermined conditions as in step a in the pulse flow mode;

c) determining an Individualized Pulse Dose Equivalent (IPDE) correlation based on data obtained from steps a and b;

d) providing the portable oxygen concentration system with the IPDE correlation; and e) using the IPDE correlation to operate the concentrator in a more efficient manner.

2. The method of claim 1, wherein titrating the patient to a predetermined blood oxygen saturation in steps a and b is performed with a pulse oximeter.

3. The method of claim 1, wherein the predetermined blood oxygen saturation is at least 90% $SaO_2$.

4. The method of claim 1, wherein the portable oxygen concentration system weighs 4 to 20 lbs.

5. The method of claim 1, wherein the one or more conditions in steps a and b is a resting condition.

6. The method of claim 1, wherein the one or more conditions in steps a and b is a ambulatory condition.

7. The method of claim 1, wherein the one or more conditions in steps a and b is a sleeping condition.

8. The method of claim 1, wherein the one or more conditions in steps a and b is a high-altitude condition.

9. A method of using a combination continuous flow and pulse flow portable oxygen concentration system with a patient, comprising:

a) providing the portable oxygen concentration system in a continuous flow mode and titrating the patient to a predetermined blood oxygen saturation using the portable oxygen concentration system at one or more predetermined conditions in the continuous flow mode;

b) providing the portable oxygen concentration system in a pulse flow mode and titrating the patient to the same predetermined blood oxygen saturation as step a using the portable oxygen concentration system at the same one or more predetermined conditions as in step a in the pulse flow mode;

c) sensing one or more conditions related to one or more of the patient and an environment of the patient;

d) determining an Individualized Pulse Dose Equivalent (IPDE) correlation to provide a predetermined blood oxygen saturation based on the sensed one or more conditions using the IPDE correlation; and e) supplying oxygen gas to the patient in a pulse flow mode at the IPDE to provide the predetermined blood oxygen saturation.

10. The method of claim 9, wherein the sensing occurs with one or more output sensors that sense one or more conditions related to one or more of the patient and the environment of the patient.

11. The method of claim 10, wherein the one or more output sensors include one or more of an ultrasonic flow sensor, a gas temperature sensor, an atmospheric pressure sensor, a humidity sensor, and a breath detect sensor.

12. The method of claim 10, wherein the portable oxygen concentration system weighs 4 to 20 lbs.

13. A combination continuous flow and pulse flow portable oxygen concentration system for use with a patient, comprising:

a) an oxygen gas generator that separates concentrated oxygen gas from ambient air;

b) an energy source that powers at least a portion of the oxygen gas generator;

c) one or more output sensors that sense one or more conditions related to one or more of the patient and an environment of the patient; and d) a control unit linked to the one or more output sensors and the oxygen gas generator to control the operation of the oxygen gas generator, the control unit using a Individualized Pulse Dose Equivalent (IPDE) correlation to supply oxygen gas to the patient in a pulse flow at an Individualized Pulse Dose Equivalent (IPDE) to provide a predetermined blood oxygen saturation based on the sensed one or more conditions.

14. The portable oxygen concentration system of claim 13, wherein the one or more output sensors include one or more of an ultrasonic flow sensor, a gas temperature sensor, an atmospheric pressure sensor, a humidity sensor, and a breath detect sensor.

15. The portable oxygen concentration system of claim 13, wherein the portable oxygen concentration system weighs 4 to 20 lbs.

* * * * *